(12) United States Patent
Choung

(10) Patent No.: US 10,073,032 B2
(45) Date of Patent: Sep. 11, 2018

(54) METHOD OF SIMULTANEOUSLY ANALYZING AMOUNT OF NUTRITIONAL COMPONENT IN VARIOUS FOODS HAVING DIFFERENT PHYSICOCHEMICAL PROPERTIES AND COMPOSITIONS BY NEAR-INFRARED REFLECTANCE SPECTROSCOPY

(71) Applicant: KNU-INDUSTRY COOPERATION FOUNDATION, Gangwon-do (KR)

(72) Inventor: Myoung-Gun Choung, Gangwon-do (KR)

(73) Assignee: KNY-INDUSTRY COOPERATION FOUNDATION, Gangwon-Do (KR)

( * ) Notice: Subject to any disclaimer, the term of this patent is extended or adjusted under 35 U.S.C. 154(b) by 189 days.

(21) Appl. No.: 15/272,696

(22) Filed: Sep. 22, 2016

(65) Prior Publication Data

US 2017/0010210 A1  Jan. 12, 2017

Related U.S. Application Data

(63) Continuation-in-part of application No. PCT/KR2014/010817, filed on Nov. 11, 2014.

(30) Foreign Application Priority Data

Mar. 28, 2014 (KR) .................. 10-2014-0036585

(51) Int. Cl.
*G01N 21/359* (2014.01)
*G01N 33/02* (2006.01)
*G01N 21/25* (2006.01)
*G01N 21/31* (2006.01)
*G01N 21/27* (2006.01)

(52) U.S. Cl.
CPC .......... *G01N 21/359* (2013.01); *G01N 21/25* (2013.01); *G01N 21/274* (2013.01); *G01N 21/31* (2013.01); *G01N 33/02* (2013.01); *G01N 2201/12* (2013.01)

(58) Field of Classification Search
CPC .. G01N 21/359; G01N 2201/12; G01N 21/25; G01N 21/274; G01N 21/31; G01N 2201/10; G01N 33/02
See application file for complete search history.

(56) References Cited

FOREIGN PATENT DOCUMENTS

| JP | 2002-090298 A | 3/2002 |
|---|---|---|
| KR | 2001-0062886 A | 7/2001 |
| KR | 10-1000889 B1 | 12/2010 |
| KR | 10-2011-0085084 A | 7/2011 |

(Continued)

OTHER PUBLICATIONS

International Search Report for PCT/KR2014/010817.

*Primary Examiner* — David Porta
*Assistant Examiner* — Faye Boosalis
(74) *Attorney, Agent, or Firm* — The PL Law Group, PLLC

(57) ABSTRACT

A method is for simultaneously analyzing nutritional component content in a plurality of various foods or agricultural sources having different ingredients and forms, that is, different physicochemical properties and compositions distributed in Korea by near-infrared reflectance spectroscopy. In particular, a method is for rapidly and accurately measuring nutritional component content in a plurality of various foods or agricultural sources having different ingredients and forms, that is, different physicochemical properties and compositions distributed in Korea by near-infrared reflectance spectroscopy.

13 Claims, 11 Drawing Sheets

(56) References Cited

FOREIGN PATENT DOCUMENTS

| KR | 10-2011-0106112 A | 9/2011 |
|---|---|---|
| KR | 10-1181315 B1 | 9/2012 |
| KR | 10-2013-0136668 A | 12/2013 |

METHOD OF SIMULTANEOUSLY ANALYZING AMOUNT OF NUTRITIONAL COMPONENT IN VARIOUS FOODS HAVING DIFFERENT PHYSICOCHEMICAL PROPERTIES AND COMPOSITIONS BY NEAR-INFRARED REFLECTANCE SPECTROSCOPY

CROSS REFERENCE TO RELATED APPLICATIONS

The present application is a continuation in part application to International Application No. PCT/KR2014/010817, with an International Filing Date of Nov. 11, 2014, which claims the benefit of Korean Patent Application No. 10-2014-0036585, filed in the Korean Intellectual Property Office on Mar. 28, 2014, the entire contents of which are incorporated herein by reference.

BACKGROUND

1. Technical Field

The present disclosure is directed to a method of simultaneously analyzing an amount of a nutritional component in various foods having different ingredients and forms, that is, different physicochemical properties and compositions by near-infrared reflectance spectroscopy.

2. Background Art

Food contains various nutrients, for example, a carbohydrate, a protein, a fat, a vitamin, a mineral, or the like, which are necessarily used to grow, develop, and maintain living organisms. From among these, the basic and important nutrients are carbohydrates, proteins, and fats, which are called the three major nutrients. These components produce energy for maintaining the life and activities of the human beings. Currently, quantitative analysis for carbohydrates, proteins, and fats contained in food is performed by using various analytical methods that vary depending on a component. Carbohydrates are analyzed by gas chromatography mass analysis (GC/MS) or AOAC used to measure carbohydrate content after subtraction; proteins are analyzed by Bradford color-comparison method or Kjeldahl test method; and fats are analyzed by Soxhlet method.

These various analytical methods specified for individual components have long been used, and provide relatively accurate results. However, they require complicated extraction and pre-treatment processes, a long analysis time, a person who is skilled in such analysis, and high analysis costs.

However, near-infrared reflectance spectroscopy (NIRS) may allow component analysis to be rapidly performed without the pre-treatment of a sample, and even after the analysis, the sample is intact without being damaged. Accordingly, the sample can be further used for other analysis. As an existing NIRS technology associated with a carbohydrate content, a protein content, and a fat content, there are rice amylase-content analysis, rice starch-content analysis, wheat-carbohydrate or protein analysis, pea-protein content analysis, perilla and peanut-protein content analysis, rice and brown rice-protein analysis, Jatropha seeds-protein and fat analysis, soybean-protein and fat analysis, potato chip-fat analysis, etc.

However, a near-infrared absorption spectrum has lower absorption intensity than an infrared absorption spectrum, absorptions may overlap due to several over tones or combination bands, and a particular absorption region due to a hydrogen bond or an intermolecular interaction may be shifted. Accordingly, it is difficult to interpret an absorption spectrum. Up until now, there are only methods of quantitatively analyzing components included in a single type of foods having an identical form, that is, an identical matrix having the same physicochemical property and composition or a particular food group that includes an identical material as a major component and an identical form.

Korean Patent No. 10-1000889 discloses a method of predicting protein contents of brown and milled rice by using wet-paddy rice, and Korean Patent No. 10-1181315 discloses a method of simultaneously measuring caffeine content and individual catechins contents in green tea leaves. However, as disclosed in the present application, a method of simultaneously analyzing an amount of a nutritional component contained in various foods having different physicochemical properties and compositions by NIRS has not been disclosed.

SUMMARY

Analyzing of nutritional components contained in various foods or agricultural sources, which are being distributed in Korea, takes relatively a long time. Also, various kinds or forms of foods cannot be simultaneously analyzed. To address these problems, provided is a method of quantitatively analyzing nutritional components, for example, carbohydrates, proteins, or fats, contained in foods having different ingredients and forms, that is, different physicochemical properties and compositions, which are being distributed in Korea, by near-infrared reflectance spectroscopy in a non-destructive, rapid manner.

An aspect of embodiments of the present disclosure provides a method of simultaneously analyzing an amount of a nutritional component in a plurality of various foods or agricultural sources having different physicochemical properties and compositions by near-infrared reflectance spectroscopy (NIRS), and in particular, to a method of simultaneously analyzing amounts of a plurality of nutritional components in a plurality of various foods or agricultural sources having different ingredients and forms, that is, different physicochemical properties and compositions by NIRS, the method including:

(1) analyzing an amount of a nutritional component contained in a plurality of various species of foods and agricultural sources having different physicochemical properties and compositions by using analytical methods of analyzing components described in the Korean Food Standard Codex;

(2) classifying the plurality of various species of foods or agricultural sources into a calibration sample set and a validation sample set;

(3) irradiating a near-infrared ray to the calibration sample set and the validation sample set to simultaneously obtain primitive near-infrared absorption spectra thereof;

(4) correcting scatter of the primitive near-infrared absorption spectrum of the calibration sample set obtained in step (3);

(5) obtaining a derivative based on the primitive absorption spectrum of which scatter has been corrected, followed by subjecting the derivative to a math treatment represented by W-X-Y-Z (W is a differentiation degree, X is a gap (nm) of wavelength used to measure a spectrum, Y is a primary smoothing to smooth the connection of the spectrum during a math treatment with respect to the gap of wavelength, Z is a secondary smoothing to smooth the connection of the spectrum during the math treatment with respect to the gap of wavelength), and performing statistical analysis by comparing component contents obtained based on the resultant derivative with content values obtained by using the analytical methods obtained in operation (1), thereby selecting primary calibration equations;

(6) validating the primary calibration equations selected in operation (5) by applying the primary calibration equations to the primitive near-infrared absorption spectra of the validation sample set obtained in operation (3) to obtain an optimal calibration equation; and (7) quantitatively analyzing the nutritional component in the plurality of various foods or agricultural sources by using the optimal calibration equation.

The nutritional component in the plurality of various foods or agricultural sources having different physicochemical properties and compositions may include at least one selected from a protein, a carbohydrate, a sugar, a fat, a fatty acid, an amino acid, an organic acid, a moisture, a vitamin, and a mineral, but is not limited thereto.

The primitive near-infrared absorption spectra may be obtained in a wavelength range of 400 nm to 2,500 nm. In general, in the case of a near-infrared absorption spectrum, an absorption spectrum corresponding to the wavelength of 800 nm to 2,500 nm is used. However, according to the present disclosure, a plurality of various foods or agricultural sources having different ingredients and forms, that is, different physicochemical properties and compositions are simultaneously measured. Accordingly, the absorption pattern corresponding to the wavelength of 400 nm to 2,500 nm including a visible light region includes information useful for content analysis. In these aspects, the wavelength may not be limited to the range of 800 to 2,500 nm.

A mode for measuring the near-infrared absorption spectrum may be any one mode selected from a diffuse reflectance mode, a transmission-reflectance mode, and a transmission mode. In one embodiment, the mode for measuring the near-infrared absorption spectrum may be a diffuse reflectance mode. However, the mode for the near-infrared absorption spectrum is not limited thereto, and any mode may be available herein as long as the near-infrared absorption spectrum is appropriately measured.

The near-infrared absorption spectrum may be measured by using various measurement modules that can be generally available. However, when a sample consists of various ingredients and forms, for example, a solid, a liquid, or a viscous semi-solid, in the case of a vertical measurement module, which is generally used, it is impossible to measure a liquid or semi-solid viscous sample.

Accordingly, the near-infrared absorption spectrum of a sample may be measured by using a horizontal direct contact food analyzer (DCFA) module, which requires an unlimited form of a sample and prevents the spill of a liquid or semi-solid sample. In the case of the horizontal DCFA module, a sample vessel is not predetermined, but may vary depending on a sample. In one embodiment, a sample may be directly analyzed while inside a plastic bag, such as a zipper bag. In one embodiment, a sample may be analyzed while directly on glass surface of the horizontal measurement module using measurement sample cup.

In the case of food or agricultural sources in the form of powder or solid lump, a sample may not have uniform physical characteristics, such as a particle size. Accordingly, to increase the level of accuracy, it is necessary to measure several portions of the sample by tens of spinning while a measurement sample cup is maintained in its vertical position. However, in the case of liquid or viscous semi-solid samples, these samples are already uniform in their original states. Accordingly, there is no need to enlarge a target portion by spinning, and it is possible to obtain a primitive absorption spectrum. Also, when a liquid and viscous sample undergoes tens of spinning while the sample is maintained in its vertical state, a moisture may be removed therefrom by a centrifugal force, leading to damage on a device, contamination on a measurement device, and a failure to obtain an accurate spectrum. Accordingly, there is a need to use a measurement vessel that allows liquid or viscous semi-solid samples to be accurately measured. Thus, a measurement vessel can be customized according to the need.

Liquid or semi-solid viscous samples may contaminate a cover or various portions of a measurement vessel. To prevent the contamination, the measurement vessel may be a cover-free small reflectance vessel. However, the measurement vessel is not limited thereto.

Regarding the method of measuring the near-infrared absorption spectrum, a reference for classifying the plurality of various foods or agricultural sources having different physicochemical properties and compositions into the calibration sample set and the validation sample set is not limited. In one or more embodiments, however, to be applied to known various foods or agricultural sources regardless of the kind and form, the calibration sample set may overall include a plurality of various foods or agricultural sources having different physicochemical properties and compositions. Accordingly, the calibration sample set may include a greater number of samples than the validation sample set. In one embodiment, the ratio of the number of samples consisting of the calibration sample set to the number of samples consisting of the validation may be in a range of 2:1 to 4:1. In one embodiment, the ratio of the number of samples consisting of the calibration sample set to the number of samples consisting of the validation may be in a range of 2:1 to 3:1. In other words, when various kinds of samples are used by controlling the number of samples consisting of the calibration sample set to be 2 to 4 times as great as that of the validation sample set, excellent analysis results may be obtained and the range of use may be extended.

The scatter correction of the near-infrared absorption spectra refers to correcting a non-linear function that distorts the correlation between a spectrum and a wet analysis value. The scatter correction may include at least one selected from standard multiplicative scatter correction (standard MSC), inverse MSC, detrend correction (a manner of removing a liner or secondary curvature from individual spectra), standard normal variate (SNV) correction, and weighted MSC.

The statistical analysis of the derivative may be multivariate regression, since the range of the near-infrared spectrum is negligible in view of change in chemical or physical properties. In one or more embodiments, the statistical analysis of the derivative may be any one selected from multiple linear regression (MLR), principal component regression (PCR), partial least squares (PLS), and modified partial least squares (MPLS). When a sample has a simple structure and a target component has a particular peak shape, MLR may be used. When absorption bands overlap and the obtained spectrum is complicated, PCR or PLS may be used. When cross-validation is used, since errors may occur in a correlation degree depending on each wavelength variable and cross validation results in the procedure of inducing the correlation between the full wavelength band and experimental values, MPLS may be used.

When the nutritional component is a carbohydrate, the scatter correction may be weighted MSC, and the math treatment may be any one selected from 1-4-1-1, 1-4-5-1, and 1-4-10-5. When the nutritional component is a protein, the scatter correction may be standard MSC, and the math treatment may be any one selected from 2-5-5-3, 2-5-10-1, and 2-6-1-1. When the nutritional component is a fat, the scatter correction may be SNV correction, and the math treatment may be any one selected from 1-1-1-1, 1-1-3-1, and 1-3-10-5. However, these math treatments are not limited thereto.

The 'terms' used for statistics herein have the following definitions.

The term "the standard error of calibration (SEC)" used herein refers to a standard error between a wet analysis value and a NIRS prediction value when a calibration set used to construct calibration equations is predicted as calibration equation.

The term "the coefficient of determination (RSQ, $R^2$)" used herein refers to an amount of a variance in a calibration set. The condition that RSQ is 1 means that 100% of the variance of components constituting calibration equation sample can be explained according to NIRS calibration equation.

The term "the standard error of cross validation (SECV)" used herein refers to a standard error between a wet analysis value and a NIRS prediction value of calibration equation food group when samples are sequentially removed in constructing calibration equation.

The term "1-variance ratio (1-VR)" used herein refers to how many times the variance of components can be explained by using NIRS calibration equation. The condition that 1-VR means that 100% (total) of the variance of components constituting calibration equation food group can be explained according to NIRS calibration equation in the procedure of cross validation.

The term "the standard error of prediction (SEP)" used herein refers to a standard error between a wet analysis value and a NIRS prediction value of an independent food group. The SEP is used to analyze an independent food group that is not used when calibration equation is constructed.

Embodiments of the present disclosure provide a method of simultaneously analyzing nutritional components contained in a plurality of various foods or agricultural sources having different physicochemical properties and compositions by near-infrared reflectance spectroscopy (NIRS). Since NIRS does require neither extracting of components contained in foods or agricultural sources nor a chemical reaction, the use of NIRS provides a non-destructive manner, and enables a simultaneous and rapid analysis of various nutritional components, for example, a protein, a carbohydrate, a sugar, a fat, a fatty acid, an amino acid, an organic acid, a moisture, a vitamin, and a mineral, contained in a plurality of various foods or agricultural sources having different physicochemical properties and compositions. Furthermore, even after the analyzing, the used foods can be collected in its original form. Accordingly, identical foods or agricultural sources can be repeatedly analyzed, or other functional components than the nutritional components can be further analyzed. Thus, this analytical method provides analysis reproducibility and enables validation of various components.

DETAILED DESCRIPTION

Figure 1:
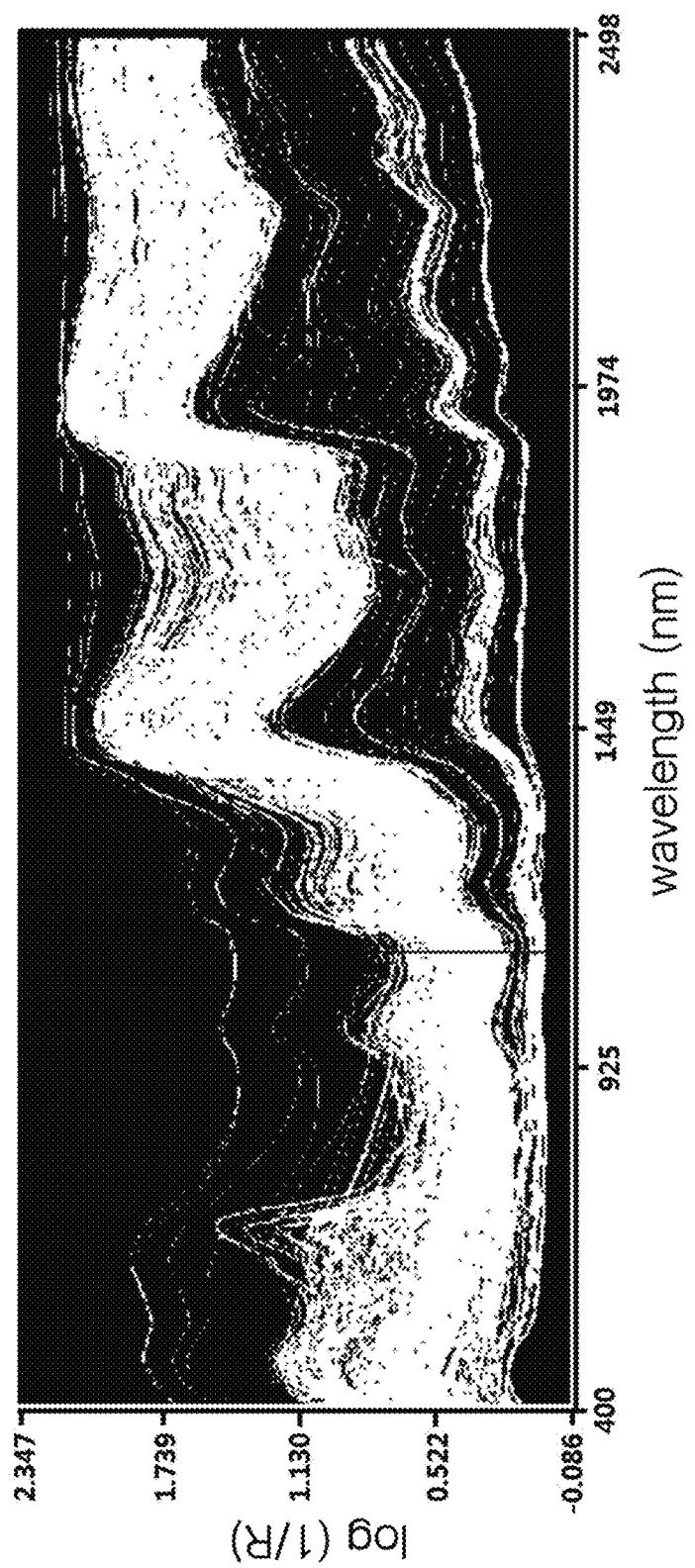
FIG. 1 shows a primitive near-infrared absorption spectrum of a calibration sample set consisting of 412 foods having different physicochemical properties and compositions, having absorption peaks at the wavelength of 986 nm, 1194 nm, and 1930 nm.

Hereinafter, embodiments of the present disclosure will be described in detail with Examples. These examples are provided herein for illustrative purpose only, and do not limit the scope of the present invention.

Example 1. Analyzing Carbohydrate Contents, Protein Contents, and Fat Contents in Foods Distributed in Korea 1) Preparation of Samples A total of 574 foods or agricultural sources having various ingredients and various forms, that is, different physicochemical properties and compositions were used as samples, including 72 kinds of cooked grains, 17 kinds of gruels, 36 kinds of stews, 52 kinds of meat or products associated therewith, 47 kinds of seafood, 62 kinds of vegetable, 106 kinds of side dishes, 13 kinds of Kimchi, 12 kinds of sources, 11 kinds of soups, 55 kinds of processed food, 20 kinds of fried food, and 45 kinds of seasonings, which were different forms as solid, liquid, or semi-solid viscous state.

For each sample used in this analysis, the sample was collected in a great quantity, and then, subjected to a homogenizing process.

The 574 foods or agricultural sources having different physicochemical properties and compositions were classified at a ratio of about 2:1 in such a manner that carbohydrate, protein, and fat contents in one sample set are respectively similar to those in the other sample set. As a result, 412 foods were classified as a calibration sample set and 162 foods were classified as a validation sample set. The calibration sample set and the validation sample set were similar to each other in terms of average content (%) in carbohydrate, protein, and fat, a content range thereof, and standard deviation (SD) (see Table 1).

TABLE 1

Comparing nutritional component contents in the calibration sample set with those in the validation sample set used in near-infrared reflectance spectroscopy (NIRS)

| | Number of foods | Nutritional components | Average (%) | Content range (%) | Standard deviation (SD) |
|---|---|---|---|---|---|
| Food for calibration | 412 | Carbohydrate | 25.201 | 0.04-90.57 | 23.718 |
| | 412 | Protein | 9.099 | 0.11-33.86 | 6.722 |
| | 412 | Fat | 6.034 | 0.02-38.96 | 7.508 |
| Food for validation | 162 | Carbohydrate | 23.331 | 0.06-88.01 | 22.054 |
| | 162 | Protein | 8.979 | 0.48-26.55 | 6.544 |
| | 162 | Fat | 5.116 | 0.03-27.42 | 5.875 |

Regarding the calibration sample set, carbohydrate, protein, and fat content ranges were 0.04 to 90.57%, 0.11 to 33.86%, and 0.02 to 38.96%, respectively. Carbohydrate, protein, and fat content ranges in the calibration sample set were included in and wider than those in the validation sample set.

2) Analyzing Carbohydrate Content, Protein Content, Fat Content, Moisture Content, and Ash Content in Food by Wet Chemical Analysis (Reference Value)

Regarding 574 foods or agricultural sources having different physicochemical properties and compositions, carbohydrate content, protein content, fat content, moisture content, and ash content were analyzed according to methods of analyzing components described in the Korean Food Standard Codex. This analysis was performed three times for each sample.

(i) Protein Content Analysis

By using a Semi-micro Kjeldahl method, nitrogen content in food was quantified, and then, the nitrogen content was converted into protein content.

A general nitrogen factor is 6.25, which is obtained based on the condition that a protein contains 16% (w/v) nitrogen. Since the protein contains, in addition to nitrogen, derivatives of purine and pyrimidine base in a nucleic acid, the protein is not a pure protein. Accordingly, the protein is called a crude protein. This analysis includes decomposition, distillation, neutralization, and titration. For each sample, with respect to the nitrogen (N) content of 2 mg to 3 mg, 0.5 g of a decomposition facilitator, 3 to 5 ml of 98% (v/v) sulfuric acid, and 1 ml of 30% (v/v) hydrogen peroxide were used. Until the carbide of the sample was not observed, the temperature was raised. When the decomposition solution turned light blue, the result was heated for 1 to 2 hours. Thereafter, the decomposition solution was cooled, and then, 20 ml of water was added thereto, and the resultant solution was connected to a distillation apparatus. 10 ml of 0.05 N sulfuric acid was added to an absorption flask included in the distillation apparatus. 2 to 3 drops of Brunswick reagent were added thereto, and an end of a cooler was sunk below a liquid surface, 25 ml of 30% sodium hydroxide solution added thereto through a small funnel, and the remaining liquid inside a receiving bowl was titrated by using 0.05N sodium hydroxide solution until the Brunswick reagent turned green. A blank test was performed in the same manner as described above (1 ml of 0.05N sulfuric acid=0.7003 mg N), and an amount of the protein was calculated according to Equation (1):

$$\text{Nitrogen (\%)} = 0.7003 \times (a-b) \times [100/\text{amount of sample (mg)}] \quad \text{Equation (1)}.$$

In Equation (1), a indicates an amount (ml) of 0.05 N sodium hydroxide consumed during neutralizing in the black test, and b indicates an amount (ml) of 0.05 N sodium hydroxide consumed during neutralizing in tests.

The obtained nitrogen content was multiplied by a nitrogen factor that varies depending on food. The result was determined as crude protein content. (see Equation (2))

$$\text{Crude protein (\%)} = N(\%) \times \text{nitrogen factor} \quad \text{Equation (2)}$$

(ii) Fat Content Analysis

To quantitatively measure fat in a sample, fat content analysis was performed in such a manner that the fat was extracted by using a Soxhlet extractor while ether was circulated therein. The fat extracted from the sample by being dissolved by ether is not limited to pure oil. For example, an organic acid, alcohols, essential oils, pigments, fat-soluble vitamins, and the like may also be extracted. However, these additionally obtained materials are in very small amounts. Accordingly, the fat that was quantified by using this method is called crude fat or ether extract. The fat content analysis is described in detail hereinafter. 2 to 10 g of each sample was placed in a cylindrical filter bed, and the sample was covered by cotton wool, and then, placed in a vessel, followed by drying in a drying device at a temperature of 100 to 105° C. for 2 to 3 hours. The dry result was cooled in a desiccator, and placed in an extraction tube of Soxhlet extractor, and a receiving bowl was filled with the sample in an amount half that of anhydrous ether, and an extraction process was performed for 8 hours. Once the extraction was competed, a cooler was separated, and the cylindrical filter bed in the extraction tube was collected by using a forceps. Then, the cooler was connected to the extraction tube, and once ether was completely moved to the extraction tube, the cooler is separated, and ether was completely evaporated by using a concentrating device to which a constant-temperature vessel was connected. An outer surface of the receiving bowl was cleaned by using gauze, and then, the receiving bowl was placed in a drying device at a temperature of 98° C. to 100° C., and dried for about 1 hour until the amount of the sample was maintained constant. Then, the result was cooled in air in a desiccator, and the weight of receiving bowl was measured. An amount of crude fat was calculated according to Equation (3):

$$\text{Crude fat (g)} = \{(W_1 - W_0)/S\} \times 100 \qquad \text{Equation (3).}$$

In Equation (3), $W_0$ indicates the weight (g) of the receiving bowl, $W_1$ indicates the weight (g) of the receiving bowl containing crude fat that had been extracted and dried, and S indicates an amount (g) of the sample collected.

(iii) Moisture Content Analysis

Moisture content was analyzed by atmospheric heating-dry method. In the atmospheric heating-dry method, moisture was considered as a unique volatile component. Each sample was atmospheric-dried at a temperature that is higher than the boiling point of water, and a decrease in the weight of the sample was considered as moisture content. The heating temperature was varied depending on the kind or property of food. In the case of animal food and protein-rich food, the heating temperature was in a range of 98-100° C.; in the case of sucrose and glucose-rich food, the heating temperature was in a range of 100-103° C.; in the case of plant food, the heating temperature was around 105° C. (100-110° C.), and in the case of grains; and the heating temperature was in a range of 110° C. or more (135° C.). The moisture content analysis will be described in detail hereinafter. 3 to 5 g of a sample was placed on a weighing dish, of which weight had been maintained constant by heating in advance, and while a cover for the weighing dish was slightly open, the weighing dish was placed in a drying device at a temperature that had been adjusted to be appropriate for the sample, and dried for 3 to 5 hours, and cooled in a desiccator for about 30 minutes. The weight of the result was measured. Then, the weighing dish was dried for 1 to 2 hours. This experiment was repeatedly performed until the weight of the result was maintained constant. Moisture content was calculated according to Equation (4):

$$\text{Moisture (g)} = (b-c)/(b-a) \times 100 \qquad \text{Equation (4).}$$

In Equation (4), a indicates a weight (g) of the weighing dish, b indicates the sum (g) of the weight of the weighing dish and the weight of the sample, and c indicates a weight (g) of the weighing dish when the weight was maintained constant after drying.

(iv) Ash Content Analysis

The ash content refers to an amount of ash when a sample was placed in an ashing container and then an ashing treatment therefor was completed at a temperature of 550° to 600° C. The ash content analysis will be described in detail hereinafter. An ashing container was strongly heated in an electric furnace at a temperature of 600° C. or more, and then, placed on a desiccator and cooled therein and weighed. This experiment was repeatedly performed until the weight of the ashing container maintained constant. Then, a sample was placed in the ashing container. In an ashing furnace, at a temperature of 550° C. to 600° C., the sample was heated for several hours until the sample turned white or gray-white. Then, the resultant sample was cooled at a temperature of 200° C., and then, placed in a desiccator and weighed. The ash content was quantified according to Equation (5):

$$\text{Ash content (g)} = \{(W_1 - W_0)/S\} \times 100 \qquad \text{Equation (5).}$$

In Equation (5), $W_0$ indicates a weight (g) of the ashing container of which amount had been maintained constant, $W_1$ indicates the sum (g) of the weight of the post-ashing ashing container and the weight of the ash content, and S indicates an amount of the sample.

(v) Carbohydrate Content Analysis

Carbohydrate content was calculated by subtracting amounts of crude protein, crude fat, moisture, and ash from 100 g of a sample. This calculation is shown in Equation (6):

$$\text{Carbohydrate (g)} = 100 \text{ g} - [\text{crude protein} + \text{crude fat} + \text{moisture} + \text{ash content}](\text{g}) \qquad \text{Equation (6).}$$

3) Analyzing Nutritional Component Content in Foods by Near-Infrared Spectrometer (i) Measuring Near-Infrared Absorption Spectrum, and Pre-Treatment The near-infrared spectrum of 574 foods or agricultural sources having different physicochemical properties and compositions, which are distributed in Korea, was obtained by using an NIRS system model 6500 spectrometer (Foss NIRS systems Inc., Silver Spring, Md.). Before analysis, for stabilization, self-diagnosis was performed by executing WinISI II (version 1.5, Foss and Infrasoft International LLC, Stage Collgeg, Pa.) software in a horizontal direct contact food analyzer (DCFA) module. Once passed through a response test, accuracy of wavelength, and a repeatability test, the spectrometer was considered as being ready for analysis. Once the stabilization test was completely performed, in a horizontal DCFA module, a small reflectance vessel that is available for a solid, liquid, or semi-solid viscous sample was half-filled with a sample, and then, a near-infrared absorption spectrum having a wavelength of 400 nm to 2,500 nm was measured.

In the present experiment, to analyze liquid and viscous semi-solid samples, a steel holder that allows a device to be forcibly, horizontally placed thereon was manufactured. The steel holder was used as a holder receiving the side surface of an NIR device. The NIR device was forced to be horizontally placed on the steel holder, and a spin module or a transport module, which had already been set up, was removed therefrom, and, after a horizontal DCFA module for the horizontal positioning of a sample was set up, a cover-free quartz measurement vessel to house a liquid and viscous semi-solid sample was manufactured and used. By doing so, without leaking or spilling of liquid or viscous semi-solid samples while in a horizontal position, the spectrum of the sample was able to be measured with reproducibility. This horizontal measurement module enables measuring of a spectrum with respect to a wide area of the liquid and viscous semi-solid sample, without leaking or spilling of liquid or viscous semi-solid samples caused by spin or transport while in a horizontal position. With reference to carbohydrate, protein, and fat contents obtained by using methods of analyzing components described in the Korean Food Standard Codex, the 574 food samples having different physicochemical properties and compositions were randomly classified at a ratio of 2:1 in such a manner that sample sets were similar to each other in terms of component content. The 574 food samples were randomly divided into a calibration food set of 412 samples used to calibrate calibration equations and a validation food set of 162 samples, and primitive near-infrared spectrum of the calibration food set and the validation food set were obtained.

Figure 2:
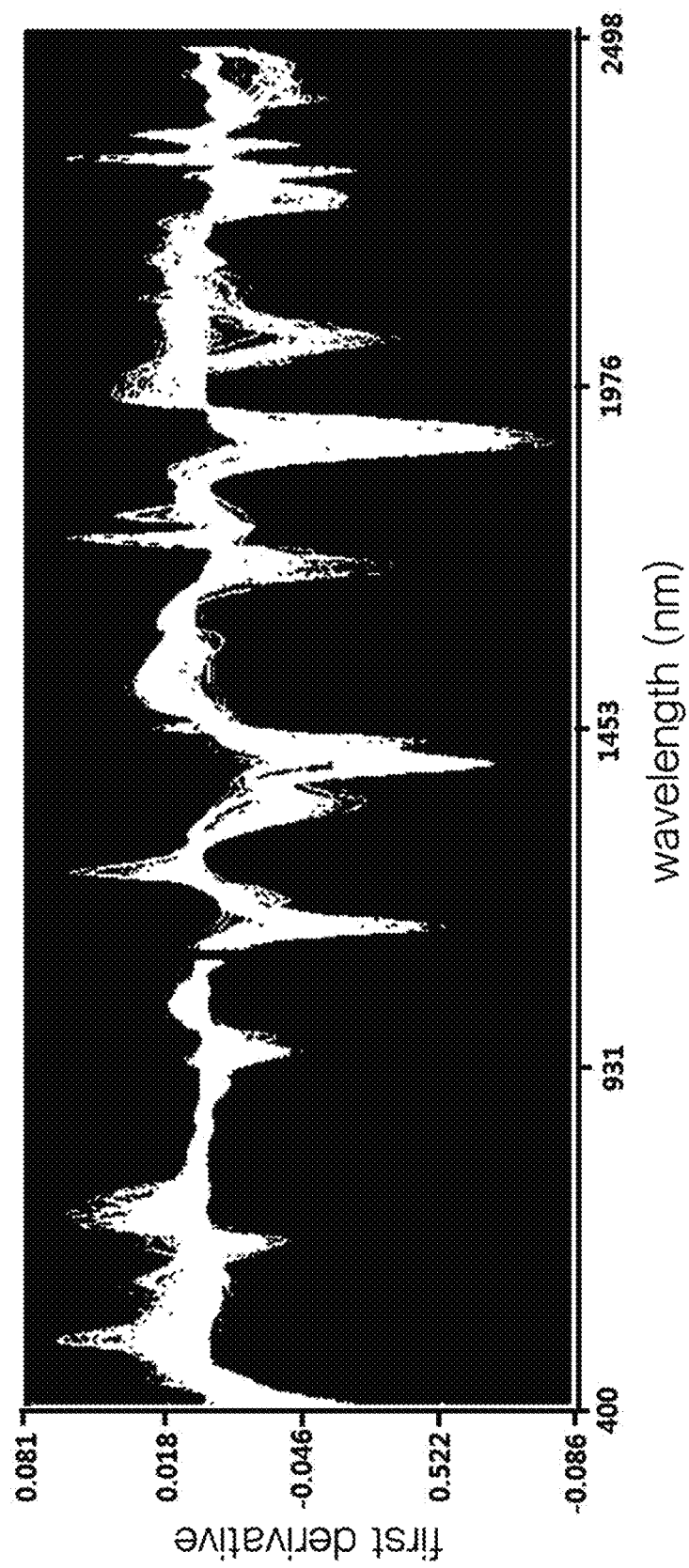
FIG. 2 shows a first derivative (1-4-5-1, standard MSC) of the primitive near-infrared absorption spectrum of the calibration sample set including 412 foods of FIG. 1, wherein large absorbance differences are present at the wavelengths of 1,144 nm, 1,398 nm, and 1,888 nm, and a C—H tertiary overtone band region associated with fats is present around the wavelength of 928 nm, an N—H region associated with proteins is present around the wavelengths of 1,020 nm, 1,510 nm, and 2,048 nm, a carbohydrate (starch)-associated region is present around the wavelengths of 1,888 nm and 2,258 nm, and a moisture-associated region is present around the wavelengths of 952 nm and 1452 nm.
Figure 3:
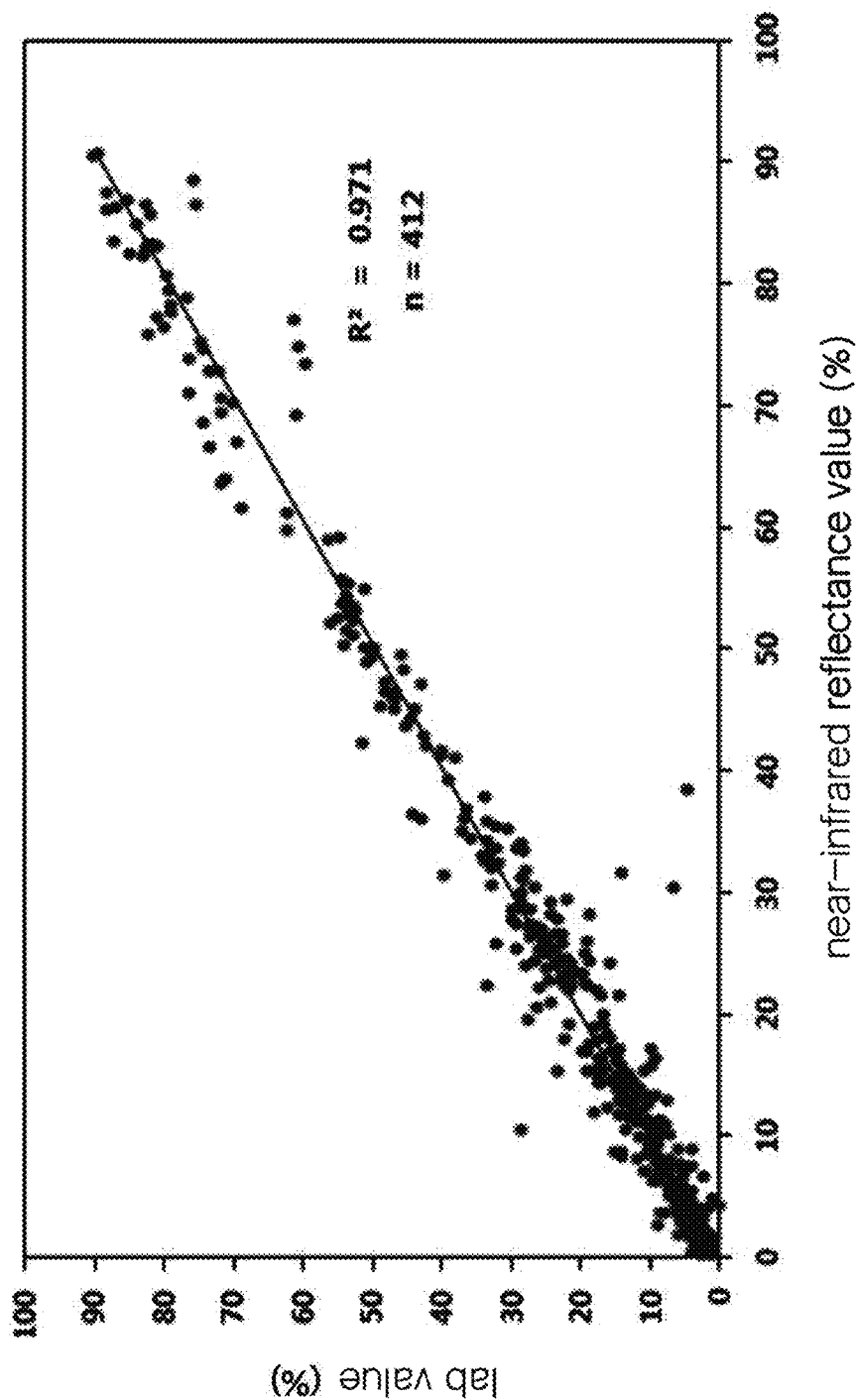
FIG. 3 shows a scatter diagram to compare a carbohydrate content of 412 foods belonging to the calibration sample set and having different physicochemical properties and compositions obtained from the near-infrared absorption spectrum thereof with a carbohydrate content measured by wet analysis.
Figure 4:
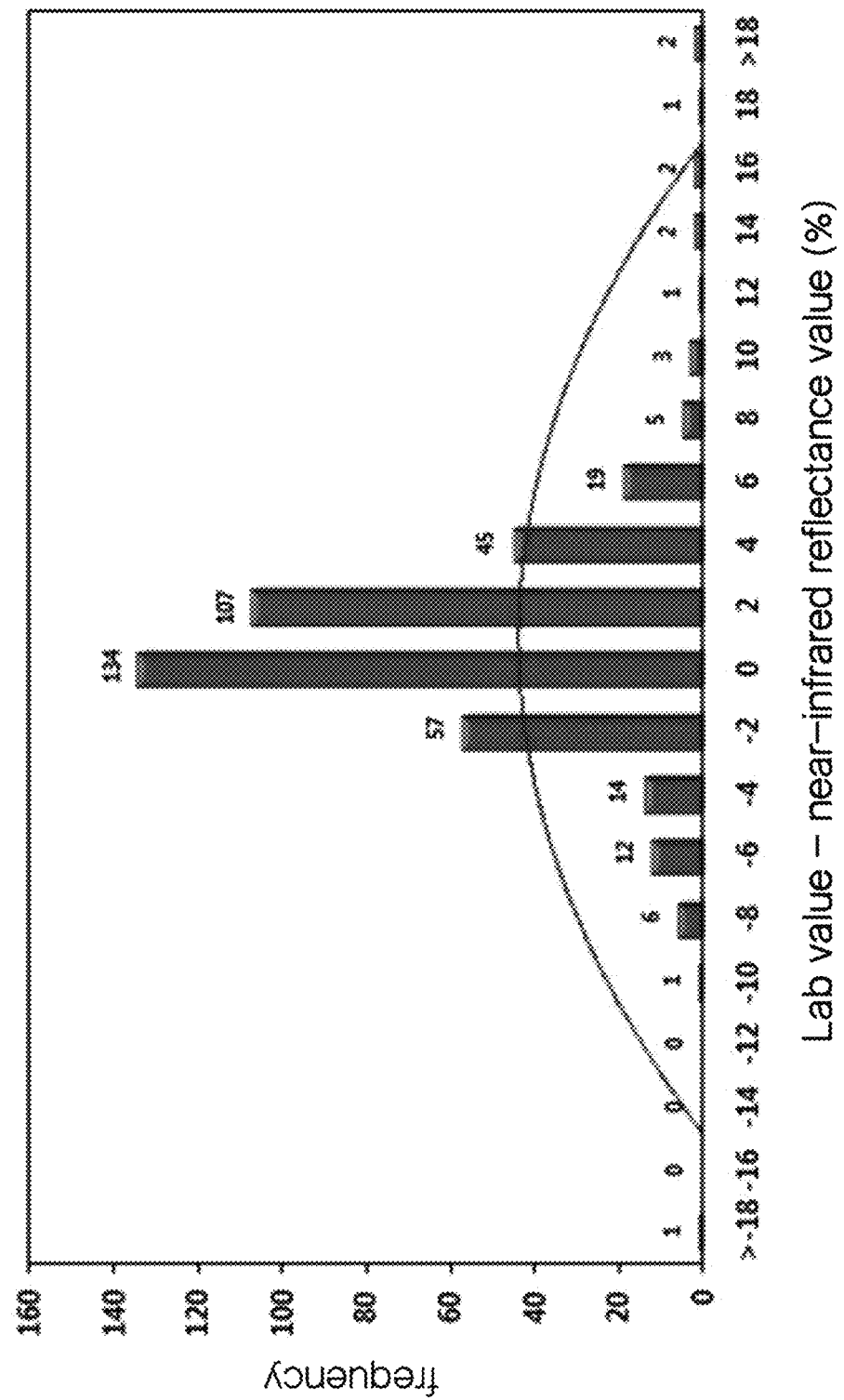
FIG. 4 shows a histogram indicating a difference between carbohydrate contents in 412 foods belonging to the calibration sample set and having different physicochemical properties and compositions obtained from the near-infrared absorption spectrum thereof with carbohydrate contents measured by wet analysis.
Figure 5:
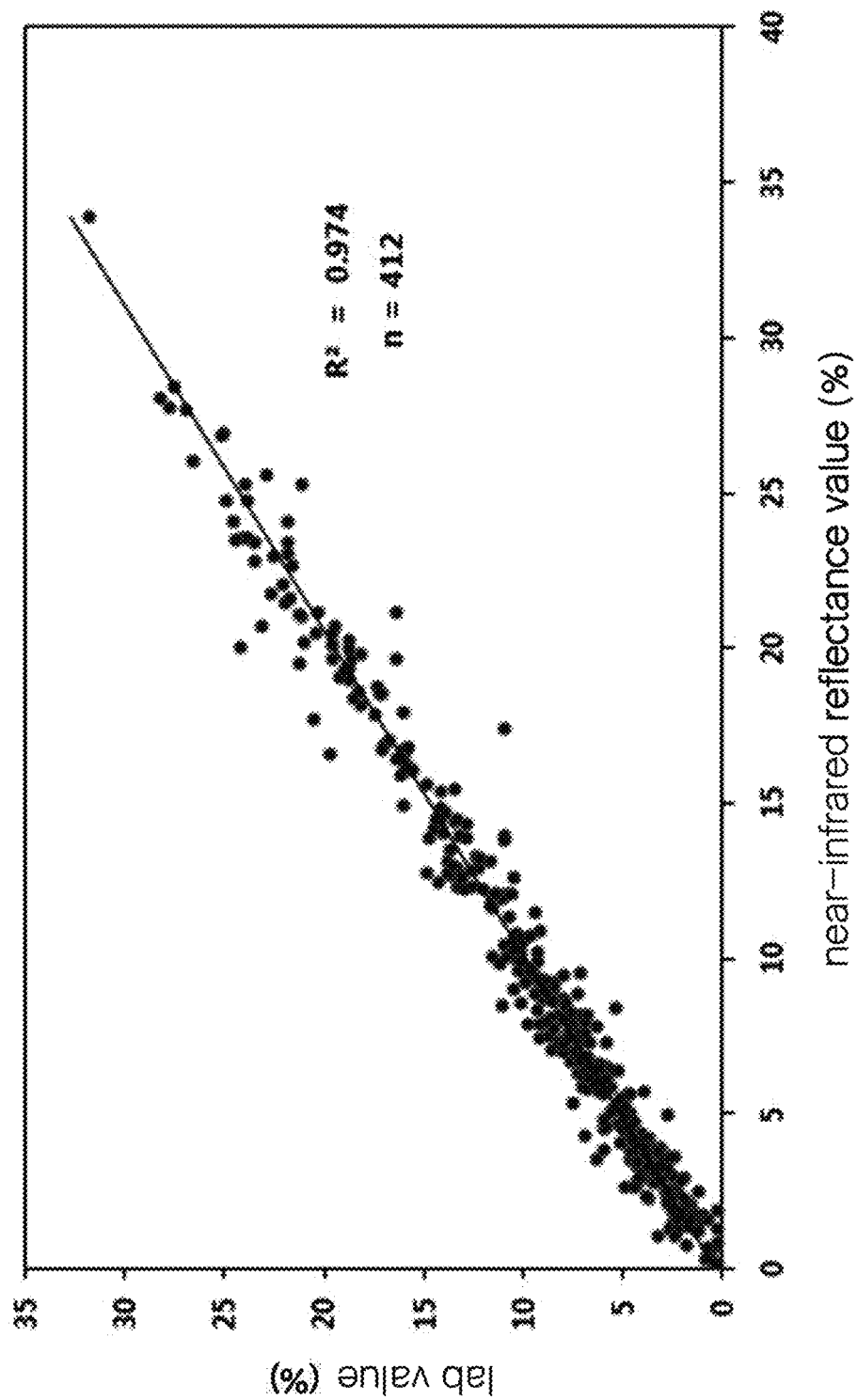
FIG. 5 shows a scatter diagram to compare protein contents in 412 foods belonging to the calibration sample set and having different physicochemical properties and compositions obtained from the near-infrared absorption spectra thereof with protein contents measured by wet analysis.
Figure 6:
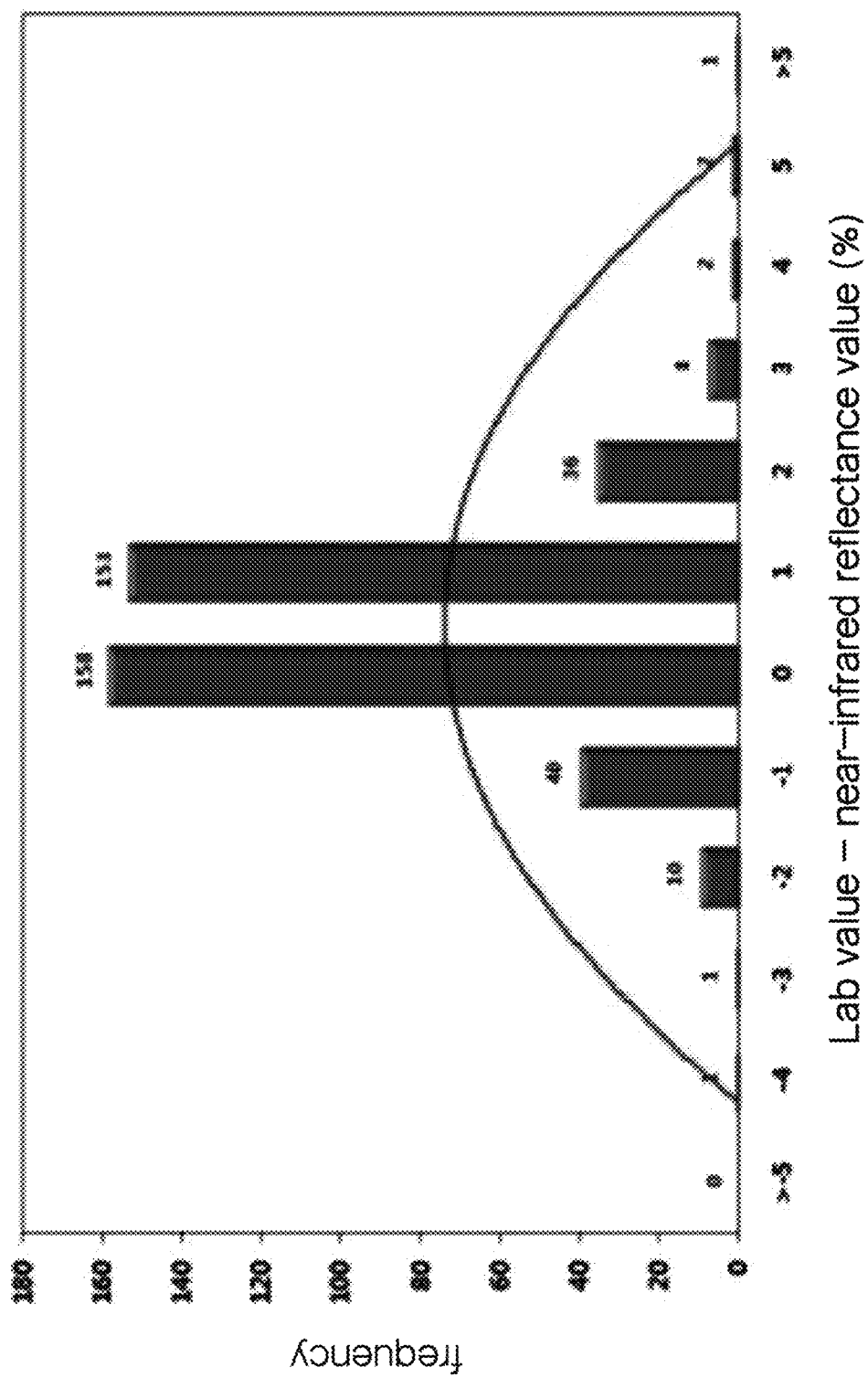
FIG. 6 shows a histogram indicating a difference between protein contents in 412 foods belonging to the calibration sample set and having different physicochemical properties and compositions obtained from the near-infrared absorption spectra thereof with protein contents measured by wet analysis.
Figure 7:
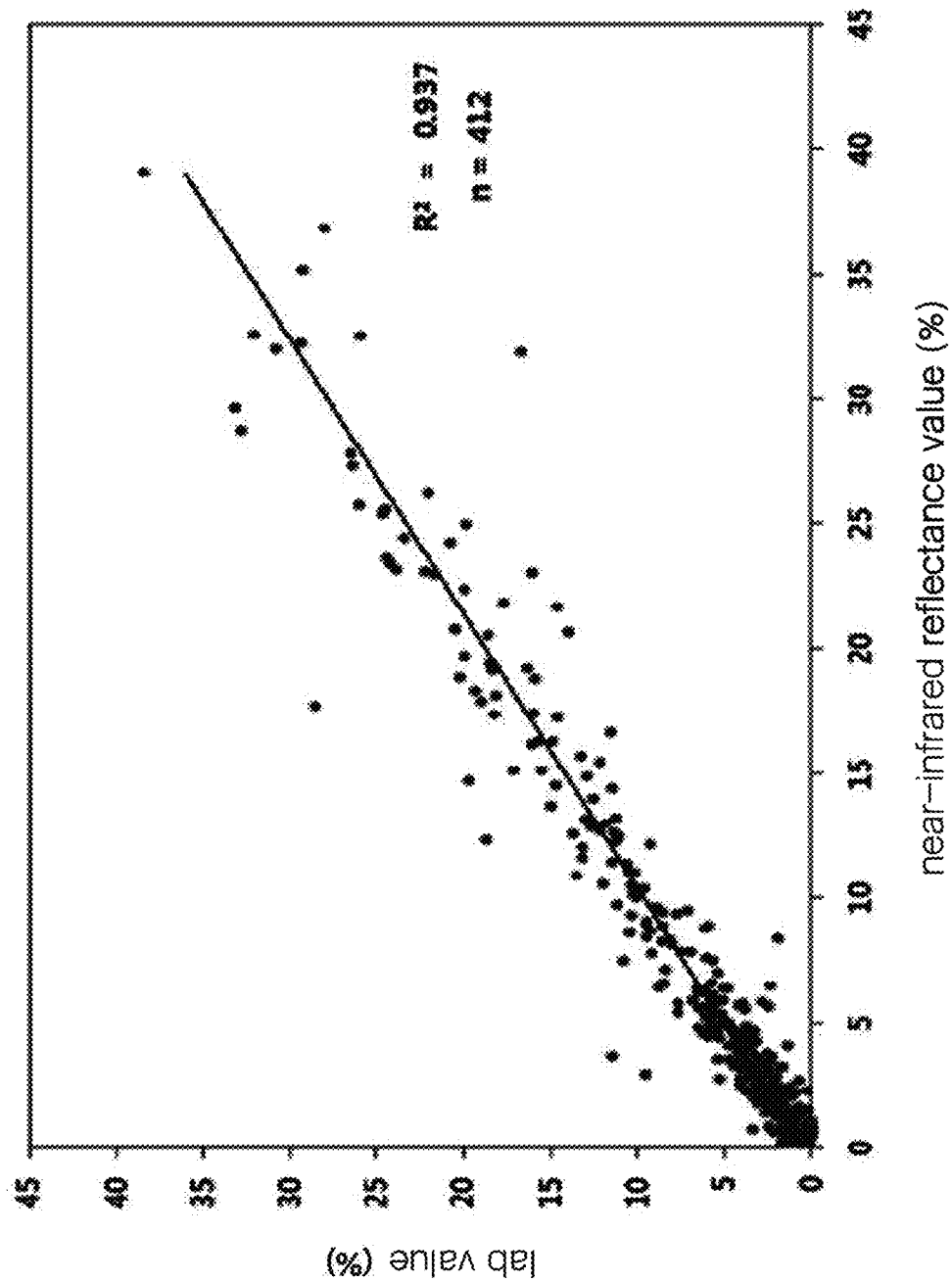
FIG. 7 shows a scatter diagram to compare a content value of fat contents in 412 foods belonging to the calibration sample set and having different physicochemical properties and compositions obtained from the near-infrared absorption spectra thereof with fat contents measured by wet analysis.
Figure 8:
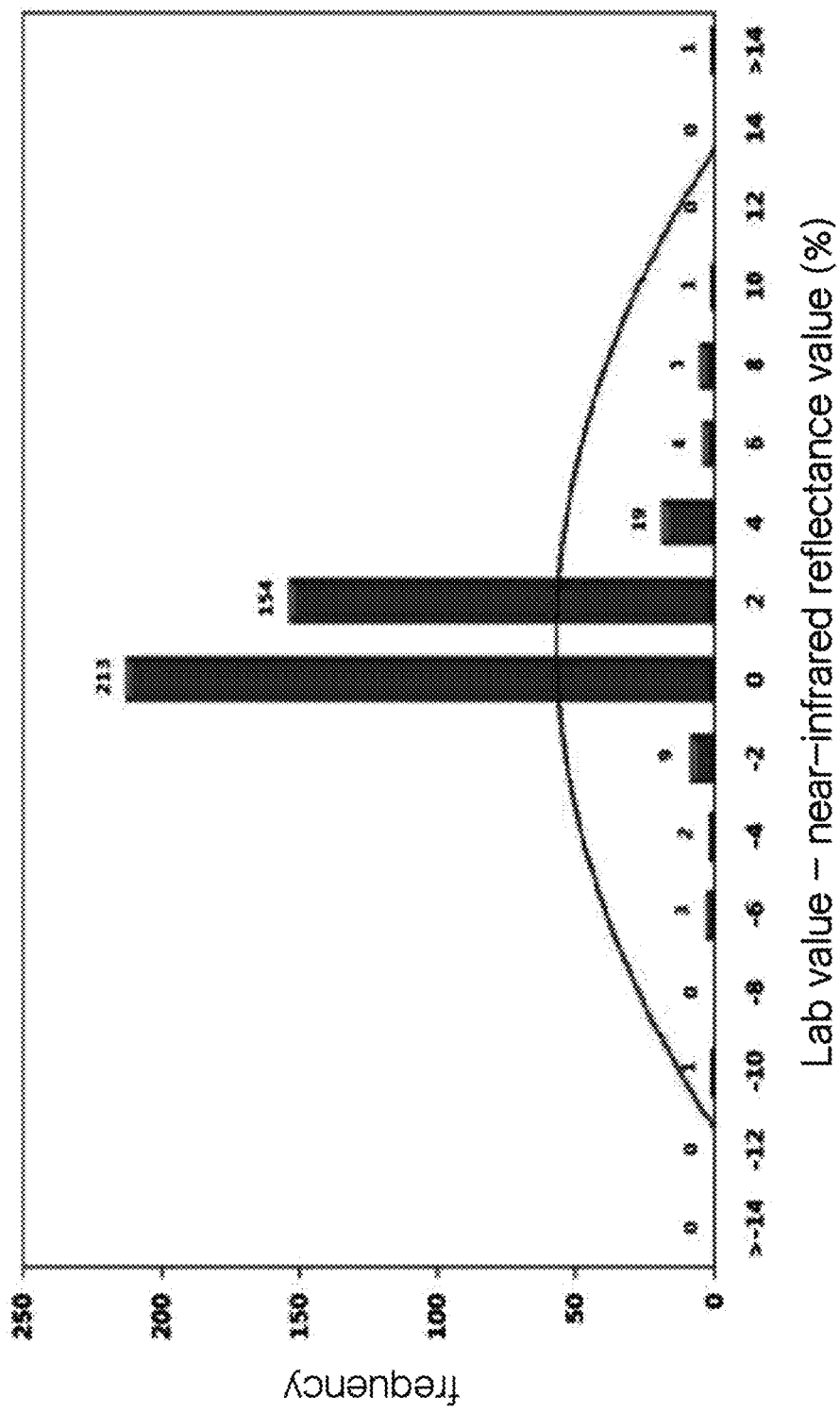
FIG. 8 shows a histogram indicating a difference between fat contents in 412 foods belonging to the calibration sample set and having different physicochemical properties and compositions obtained from the near-infrared absorption spectra thereof with fat contents measured by wet analysis.

(ii) Measuring Near-Infrared Spectrum and Constructing Calibration Equations 412 foods or agricultural sources having different physicochemical properties and compositions were used to design calibration equations, and the absorption spectra thereof having a wavelength of 400 nm to 2,500 nm was obtained (see FIG. 1). The near-infrared spectroscopic spectrum is obtainable independently from the form of a sample. However, the base line therefor is changed when absorption bands overlap, chemical components of a measurement material, or physical properties of the size of particles and the density. To reduce the change and to separate overlapping wavelengths, the math treatment was performed. FIG. 2 shows a diagram that is obtained by pre-math treating the primitive near-infrared absorption spectrum of FIG. 1. In detail, standard MSC was used to correct scatter induced due to the difference in the size of particles, an error caused by overlapping in each spectrum region was differentiated to obtain 1st derivatives (4 nm gap, 5-point smoothing, 1-point second smoothing), and as one of regression methods, a modified partial least squares (MPLS) method was used to correct the spectrum.

Regarding the MPLS, since, when the correlation between the result obtained based on the whole wavelength (400 nm to 2,500 nm) of near-infrared absorption spectrum and the result obtained by analyzing amounts of nutritional components obtained by using general test methods described in the Korean Food Standard Codex was induced by using cross validation, an optimal factor is determined to prevent overfilling and to increase accuracy, the change in the base line in the spectrum and the effects caused by the overlapping may be minimized, leading to a great coefficient of determination (RSQ, $R^2$). Based on the primitive spectrum (log 1/R), and 1st derivatives ($D^1$ log 1/R) and 2nd derivatives ($D^2$ log 1/R) spectra, various scatter correction and math treatments were used to construct NIRS calibration equations with respect to carbohydrate content, protein content, and fat content while noise and bias, occurring due to overlapping in a region of the spectrum, were minimized. Calibration equations were screened based on statistic values of standard error of calibration (SEC), coefficient of determination (coefficient of determination; RSQ, $R^2$), standard error of cross validation (SECV), and 1-VR (one minus the radio of unexplained variance to total variance).

In the primitive spectrum of 412 foods or agricultural sources for calibration, absorption peaks were present in wavelengths of 986 nm, 1,194 nm, and 1,930 nm; and in the first derivative thereof, unlike the primitive spectrum, at most wavelengths, there were small absorption intensity differences and, at wavelengths of 1,144 nm, 1398 nm, and 1,888 nm, there were great absorption intensity differences. There were absorption intensity differences in the tertiary overtone band of a C—H functional group in a wavelength region around 928 nm associated with a fat, in wavelength regions of 1,020, 1,510, and 2,048 nm corresponding to an N—H functional group associated with a protein, in wavelength regions of 1,888, and 2,258 nm associated with starch that is carbohydrate, and in wavelength regions of 952 and 1,452 nm corresponding to O—H (moisture). These wavelength regions were useful for constructing calibration equations.

The first derivative spectrum of 412 foods was used to obtain an NIRS calibration equation that is optimal to analyze carbohydrate content, protein content, and fat content in foods or agricultural sources distributed in Korea, and first, MPLS was applied and then, various math treatments and scatter correction were used. The optimal calibration equation was selected by using a calibration equation in which the coefficient of determination ($R^2$) value for calibration was near 1, the standard error of calibration (SEC) value was small, in the case of the cross validation, the 1-variance ratio (1-VR) value was great, and the standard error of cross validation (SECV) value was small.

An optimal NIRS calibration equation for carbohydrate, protein, and fat in foods or agricultural sources distributed in Korea was selected by using the coefficient of determination and the calibration equation standard error (SEC) value between component contents obtained by using general test methods described in the Korean Food Standard Codex and those obtained by the near-infrared analysis. Carbohydrate, protein, and fat contents in 412 foods or agricultural sources having different physicochemical properties and compositions obtained by using near-infrared absorption spectrum thereof were compared with carbohydrate, protein, and fat contents measured by using wet chemical analysis. Results thereof are shown in scatter diagrams and histograms of FIGS. 3 to 8.

TABLE 2

An example of selecting calibration equation candidates for carbohydrate content analysis based on the near-infrared absorption spectra of 412 foods or agricultural sources.

| Equation File | Math treatment | Scatter correction method | Number of samples | Calibration | | Cross validation | |
|---|---|---|---|---|---|---|---|
| | | | | $SEC^a$ | $R^{2\ b}$ | $1\text{-}VR^c$ | $SECV^d$ |
| 7 | 0-0-1-1 | Inverse MSC | 412 | 5.520 | 0.946 | 0.932 | 6.199 |
| 8 | 0-0-2-1 | None | 412 | 5.332 | 0.949 | 0.941 | 5.764 |
| 15 | 0-0-3-1 | None | 412 | 5.332 | 0.949 | 0.941 | 5.756 |
| 24 | 0-0-4-1 | SNV only | 412 | 4.795 | 0.959 | 0.947 | 5.448 |
| 29 | 0-0-5-1 | Weighted MSC | 412 | 4.525 | 0.964 | 0.957 | 4.940 |
| 30 | 0-0-6-1 | Weighted MSC | 412 | 4.628 | 0.962 | 0.956 | 4.998 |
| 31 | 0-0-7-1 | Weighted MSC | 412 | 4.543 | 0.963 | 0.957 | 4.946 |
| 32 | 0-0-8-1 | Weighted MSC | 412 | 4.559 | 0.963 | 0.957 | 4.933 |
| 33 | 0-0-9-1 | Weighted MSC | 412 | 4.748 | 0.960 | 0.955 | 5.058 |
| 34 | 0-0-10-1 | Weighted MSC | 412 | 4.729 | 0.960 | 0.954 | 5.066 |
| 38 | 0-0-1-2 | Detrend only | 412 | 4.744 | 0.959 | 0.947 | 5.482 |
| 44 | 0-0-1-3 | SNV only | 412 | 4.786 | 0.959 | 0.947 | 5.440 |
| 50 | 0-0-1-5 | SNV and Detrend | 412 | 4.605 | 0.962 | 0.952 | 5.217 |

TABLE 2-continued

An example of selecting calibration equation candidates for carbohydrate content analysis based on the near-infrared absorption spectra of 412 foods or agricultural sources.

| Equation | File | Math treatment | Scatter correction method | Number of samples | Calibration SEC[a] | R²[b] | Cross validation 1-VR[c] | SECV[d] |
|---|---|---|---|---|---|---|---|---|
| 57 | | 0-0-5-5 | SNV and Detrend | 412 | 4.620 | 0.962 | 0.951 | 5.225 |
| 68 | | 0-1-1-1 | Weighted MSC | 412 | 4.617 | 0.962 | 0.956 | 4.985 |
| 75 | | 0-1-1-5 | Weighted MSC | 412 | 4.525 | 0.964 | 0.957 | 4.940 |
| 78 | | 0-1-5-1 | SNV and Detrend | 412 | 4.605 | 0.962 | 0.952 | 5.217 |
| 89 | | 0-1-10-5 | Weighted MSC | 412 | 4.656 | 0.961 | 0.956 | 5.001 |
| 96 | | 0-2-1-1 | Weighted MSC | 412 | 4.617 | 0.962 | 0.956 | 4.985 |
| 103 | | 0-2-5-2 | Weighted MSC | 412 | 4.622 | 0.962 | 0.956 | 4.992 |
| 110 | | 0-2-10-5 | Weighted MSC | 412 | 4.656 | 0.961 | 0.956 | 5.001 |
| 115 | | 0-3-1-1 | Detrend only | 412 | 4.773 | 0.960 | 0.946 | 5.486 |
| 123 | | 0-3-5-2 | Standard MSC | 412 | 4.796 | 0.959 | 0.949 | 5.365 |
| 128 | | 0-3-10-8 | SNV only | 412 | 4.885 | 0.958 | 0.946 | 5.527 |
| 135 | | 0-4-5-1 | SNV only | 412 | 4.796 | 0.959 | 0.948 | 5.400 |
| 145 | | 0-5-5-1 | Weighted MSC | 412 | 4.525 | 0.964 | 0.957 | 4.940 |
| 148 | | 0-6-5-1 | SNV and Detrend | 412 | 4.605 | 0.962 | 0.952 | 5.217 |
| 158 | | 0-7-1-5 | Standard MSC | 412 | 4.795 | 0.959 | 0.949 | 5.365 |
| 163 | | 0-8-5-1 | SNV only | 412 | 4.796 | 0.959 | 0.948 | 5.400 |
| 169 | | 0-9-1-5 | SNV and Detrend | 412 | 4.605 | 0.962 | 0.952 | 5.217 |
| 176 | | 0-10-5-1 | SNV and Detrend | 412 | 4.605 | 0.962 | 0.952 | 5.217 |
| 183 | | 1-1-1-1 | SNV and Detrend | 412 | 4.320 | 0.967 | 0.954 | 5.068 |
| 193 | | 1-1-1-2 | Standard MSC | 412 | 4.408 | 0.965 | 0.956 | 4.996 |
| 200 | | 1-1-1-3 | Standard MSC | 412 | 4.419 | 0.965 | 0.956 | 4.998 |
| 205 | | 1-1-1-4 | SNV only | 412 | 4.389 | 0.966 | 0.955 | 5.036 |
| 211 | | 1-1-1-5 | SNV and Detrend | 412 | 4.152 | 0.969 | 0.957 | 4.898 |
| 221 | | 1-1-1-6 | Standard MSC | 412 | 4.177 | 0.969 | 0.957 | 4.911 |
| 226 | | 1-1-1-10 | SNV only | 412 | 4.323 | 0.967 | 0.957 | 4.911 |
| 232 | | 1-2-1-1 | SNV and Detrend | 412 | 4.227 | 0.968 | 0.956 | 4.980 |
| 240 | | 1-2-5-1 | SNV only | 412 | 4.409 | 0.965 | 0.955 | 5.047 |
| 248 | | 1-2-10-5 | Detrend only | 412 | 4.367 | 0.966 | 0.953 | 5.122 |
| 257 | | 1-3-1-1 | Weighted MSC | 412 | 4.523 | 0.964 | 0.959 | 4.806 |
| 262 | | 1-3-5-1 | Detrend only | 412 | 4.530 | 0.964 | 0.952 | 5.202 |
| 268 | | 1-3-10-8 | SNV only | 412 | 4.231 | 0.968 | 0.957 | 4.942 |
| 273 | | 1-2-2-2 | Standard MSC | 412 | 4.313 | 0.967 | 0.956 | 4.987 |
| 279 | | 1-4-1-1 | Weighted MSC | 412 | 4.530 | 0.964 | 0.959 | 4.817 |
| 286 | | 1-4-5-1 | Weighted MSC | 412 | 4.066 | 0.971 | 0.959 | 4.685 |
| 293 | | 1-4-10-5 | Weighted MSC | 412 | 4.177 | 0.969 | 0.961 | 4.706 |
| 299 | | 1-5-1-5 | Standard MSC | 412 | 4.185 | 0.969 | 0.957 | 4.920 |
| 306 | | 1-5-5-10 | Standard MSC | 412 | 4.238 | 0.968 | 0.957 | 4.920 |
| 320 | | 1-6-5-1 | Standard MSC | 412 | 4.202 | 0.969 | 0.957 | 4.923 |
| 327 | | 1-7-1-5 | Standard MSC | 412 | 4.208 | 0.969 | 0.957 | 4.923 |
| 342 | | 1-8-1-5 | Weighted MSC | 412 | 4.146 | 0.969 | 0.961 | 4.699 |
| 348 | | 1-9-5-1 | Standard MSC | 412 | 4.225 | 0.968 | 0.957 | 4.919 |
| 356 | | 1-10-5-1 | Weighted MSC | 412 | 4.168 | 0.969 | 0.961 | 4.705 |
| 362 | | 2-1-1-1 | Standard MSC | 412 | 4.379 | 0.966 | 0.942 | 5.704 |
| 370 | | 2-1-5-3 | Weighted MSC | 412 | 4.323 | 0.967 | 0.955 | 5.058 |
| 376 | | 2-1-10-8 | Standard MSC | 412 | 4.152 | 0.969 | 0.957 | 4.894 |
| 383 | | 2-2-5-1 | Standard MSC | 412 | 4.315 | 0.967 | 0.955 | 4.894 |
| 391 | | 2-3-5-5 | Weighted MSC | 412 | 4.342 | 0.966 | 0.958 | 4.877 |
| 396 | | 2-4-4-1 | Detrend only | 412 | 4.252 | 0.968 | 0.953 | 5.127 |
| 404 | | 2-5-1-5 | Standard MSC | 412 | 4.314 | 0.967 | 0.957 | 4.940 |
| 412 | | 2-6-5-4 | Weighted MSC | 412 | 4.280 | 0.967 | 0.958 | 4.835 |
| 419 | | 2-7-1-5 | Weighted MSC | 412 | 4.205 | 0.969 | 0.960 | 4.717 |
| 426 | | 2-8-10-5 | Weighted MSC | 412 | 4.242 | 0.968 | 0.960 | 4.721 |
| 433 | | 2-9-5-3 | Weighted MSC | 412 | 4.255 | 0.968 | 0.961 | 4.686 |
| 436 | | 2-10-10-1 | SNV and Detrend | 412 | 4.397 | 0.966 | 0.956 | 4.985 |

[a]SEC: Standard error of calibration
[b]R²: Coefficient of determination in calibration
[c]1-VR: 1-variance ratio (one minus the ratio of unexplained variance to total variance)
[d]SECV: Standard error of cross-validation

TABLE 3

An example of selecting calibration equation candidates for protein content analysis based on the near-infrared absorption spectra of 412 foods or agricultural sources.

| Equation file | Math treatment | Scatter correction method | Number of samples | Calibration SEC[a] | Calibration $R^2$ [b] | Cross validation 1-VR[c] | Cross validation SECV[d] |
|---|---|---|---|---|---|---|---|
| 2 | 0-0-1-1 | SNV and Detrend | 412 | 1.728 | 0.934 | 0.897 | 2.160 |
| 12 | 0-0-2-1 | Standard MSC | 412 | 1.723 | 0.934 | 0.905 | 2.076 |
| 20 | 0-0-3-1 | Weighted MSC | 412 | 1.892 | 0.921 | 0.906 | 2.064 |
| 26 | 0-0-3-2 | Standard MSC | 412 | 1.729 | 0.934 | 0.904 | 2.083 |
| 30 | 0-0-3-3 | SNV and Detrend | 412 | 1.741 | 0.933 | 0.896 | 2.170 |
| 40 | 0-0-3-4 | Standard MSC | 412 | 1.742 | 0.933 | 0.903 | 2.096 |
| 44 | 0-0-3-5 | SNV and Detrend | 412 | 1.754 | 0.932 | 0.895 | 2.177 |
| 54 | 0-0-4-1 | Standard MSC | 412 | 1.733 | 0.934 | 0.904 | 2.087 |
| 58 | 0-0-5-1 | SNV and Detrend | 412 | 1.748 | 0.932 | 0.895 | 2.174 |
| 68 | 1-1-1-1 | Standard MSC | 412 | 1.269 | 0.964 | 0.933 | 1.741 |
| 73 | 1-1-1-2 | SNV only | 412 | 1.256 | 0.965 | 0.929 | 1.788 |
| 82 | 1-1-1-3 | Standard MSC | 412 | 1.230 | 0.967 | 0.941 | 1.628 |
| 89 | 1-1-1-4 | Standard MSC | 412 | 1.233 | 0.966 | 0.944 | 1.594 |
| 96 | 1-1-1-5 | Standard MSC | 412 | 1.244 | 0.966 | 0.943 | 1.610 |
| 103 | 1-1-2-1 | Standard MSC | 412 | 1.264 | 0.965 | 0.936 | 1.707 |
| 110 | 1-4-4-1 | Standard MSC | 412 | 1.248 | 0.966 | 0.943 | 1.600 |
| 117 | 1-5-3-1 | Standard MSC | 412 | 1.250 | 0.965 | 0.943 | 1.604 |
| 124 | 1-6-4-1 | Standard MSC | 412 | 1.259 | 0.965 | 0.943 | 1.602 |
| 131 | 1-7-5-3 | Standard MSC | 412 | 1.266 | 0.965 | 0.943 | 1.609 |
| 138 | 1-8-4-1 | Standard MSC | 412 | 1.268 | 0.964 | 0.943 | 1.610 |
| 145 | 1-9-6-4 | Standard MSC | 412 | 1.294 | 0.963 | 0.940 | 1.646 |
| 152 | 1-10-10-1 | Standard MSC | 412 | 1.344 | 0.960 | 0.939 | 1.656 |
| 159 | 1-2-1-1 | Standard MSC | 412 | 1.264 | 0.965 | 0.936 | 1.707 |
| 166 | 1-2-5-10 | Standard MSC | 412 | 1.298 | 0.963 | 0.940 | 1.644 |
| 173 | 1-2-10-5 | Standard MSC | 412 | 1.298 | 0.963 | 0.940 | 1.644 |
| 180 | 1-3-1-1 | Standard MSC | 412 | 1.230 | 0.967 | 0.941 | 1.628 |
| 187 | 1-3-5-1 | Standard MSC | 412 | 1.250 | 0.965 | 0.943 | 1.604 |
| 190 | 1-3-1-10 | Standard MSC | 412 | 1.301 | 0.963 | 0.940 | 1.641 |
| 195 | 2-1-1-1 | Standard MSC | 412 | 1.409 | 0.956 | 0.864 | 2.478 |
| 202 | 2-1-10-1 | Standard MSC | 412 | 1.146 | 0.971 | 0.934 | 1.721 |
| 206 | 2-1-10-5 | Standard MSC | 412 | 1.137 | 0.971 | 0.934 | 1.731 |
| 207 | 2-1-10-10 | SNV and Detrend | 412 | 1.201 | 0.968 | 0.935 | 1.719 |
| 213 | 2-2-4-2 | Standard MSC | 412 | 1.249 | 0.965 | 0.926 | 1.828 |
| 220 | 2-2-10-5 | Standard MSC | 412 | 1.141 | 0.971 | 0.935 | 1.713 |
| 223 | 2-2-10-10 | SNV only | 412 | 1.203 | 0.968 | 0.934 | 1.728 |
| 229 | 2-3-2-1 | Standard MSC | 412 | 1.205 | 0.968 | 0.924 | 1.857 |
| 247 | 2-4-4-10 | Standard MSC | 412 | 1.181 | 0.969 | 0.935 | 1.708 |
| 250 | 2-5-1-1 | SNV only | 412 | 1.179 | 0.969 | 0.930 | 1.781 |
| 259 | 2-5-5-3 | Standard MSC | 412 | 1.080 | 0.974 | 0.940 | 1.645 |
| 270 | 2-5-10-1 | Standard MSC | 412 | 1.183 | 0.969 | 0.936 | 1.705 |
| 277 | 2-6-1-1 | Standard MSC | 412 | 1.136 | 0.971 | 0.935 | 1.715 |
| 282 | 2-6-5-2 | SNV only | 412 | 1.144 | 0.971 | 0.935 | 1.708 |
| 291 | 2-6-10-5 | Standard MSC | 412 | 1.184 | 0.969 | 0.936 | 1.696 |
| 298 | 2-7-1-1 | Standard MSC | 412 | 1.150 | 0.971 | 0.935 | 1.715 |
| 305 | 2-7-10-5 | Standard MSC | 412 | 1.193 | 0.968 | 0.937 | 1.692 |
| 310 | 2-8-1-1 | SNV only | 412 | 1.179 | 0.969 | 0.934 | 1.732 |
| 316 | 2-8-10-5 | SNV and Detrend | 412 | 1.238 | 0.966 | 0.930 | 1.774 |
| 323 | 2-9-1-1 | SNV and Detrend | 412 | 1.186 | 0.969 | 0.934 | 1.726 |
| 337 | 2-10-10-1 | SNV and Detrend | 412 | 1.260 | 0.965 | 0.931 | 1.767 |

[a]SEC: standard error of calibration
[b]$R^2$: coefficient of determination in calibration
[c]1-VR: 1-variance ratio (One minus the ratio of unexplained variance to total variance)
[d]SECV: standard error of cross validation (Standard error of cross-validation)

TABLE 4

An example of selecting calibration equation candidates for fat content analysis based on the near-infrared absorption spectra of 412 foods or agricultural sources.

| Equation File | Math treatment | Scatter correction method | n | Calibration SEC[a] | Calibration $R^2$ [b] | Cross-validation 1-VR[c] | Cross-validation SECV[d] |
|---|---|---|---|---|---|---|---|
| 3 | 0-0-1-1 | SNV only | 412 | 2.746 | 0.866 | 0.878 | 2.621 |
| 8 | 0-0-2-1 | None | 412 | 2.300 | 0.906 | 0.900 | 2.376 |
| 20 | 0-0-3-1 | Weighted MSC | 412 | 2.344 | 0.903 | 0.885 | 2.549 |
| 22 | 0-0-3-2 | None | 412 | 2.300 | 0.906 | 0.900 | 2.377 |
| 33 | 0-0-3-3 | Standard MSC | 412 | 2.203 | 0.914 | 0.900 | 2.374 |

TABLE 4-continued

An example of selecting calibration equation candidates for fat content analysis based on the near-infrared absorption spectra of 412 foods or agricultural sources.

| Equation File | Math treatment | Scatter correction method | n | Calibration SEC[a] | R²[b] | Cross-validation 1-VR[c] | SECV[d] |
|---|---|---|---|---|---|---|---|
| 46 | 0-0-3-5 | Detrend only | 412 | 2.178 | 0.916 | 0.910 | 2.256 |
| 58 | 0-1-1-1 | SNV and Detrend | 412 | 2.068 | 0.924 | 0.906 | 2.307 |
| 66 | 1-1-1-1 | SNV only | 412 | 1.890 | 0.937 | 0.914 | 2.204 |
| 73 | 1-1-1-2 | SNV only | 412 | 1.936 | 0.934 | 0.915 | 2.194 |
| 80 | 1-1-1-3 | SNV only | 412 | 2.050 | 0.925 | 0.912 | 2.234 |
| 88 | 1-1-2-1 | Detrend only | 412 | 2.005 | 0.929 | 0.914 | 2.202 |
| 94 | 1-1-3-1 | SNV only | 412 | 2.050 | 0.925 | 0.912 | 2.234 |
| 103 | 1-1-4-1 | Standard MSC | 412 | 1.966 | 0.931 | 0.912 | 2.232 |
| 107 | 1-1-5-1 | SNV and Detrend | 412 | 1.993 | 0.930 | 0.914 | 2.205 |
| 113 | 1-1-2-2 | None | 412 | 1.999 | 0.929 | 0.916 | 2.180 |
| 122 | 1-1-2-10 | SNV only | 412 | 2.014 | 0.928 | 0.910 | 2.261 |
| 129 | 1-1-3-2 | SNV only | 412 | 1.981 | 0.930 | 0.913 | 2.215 |
| 135 | 1-1-3-3 | SNV and Detrend | 412 | 1.983 | 0.930 | 0.914 | 2.204 |
| 152 | 1-2-2-5 | Standard MSC | 412 | 1.977 | 0.931 | 0.911 | 2.248 |
| 166 | 1-3-2-1 | Standard MSC | 412 | 1.963 | 0.932 | 0.911 | 2.236 |
| 173 | 1-3-5-2 | Standard MSC | 412 | 1.979 | 0.931 | 0.911 | 2.247 |
| 178 | 1-3-10-5 | SNV only | 412 | 1.987 | 0.930 | 0.910 | 2.253 |
| 186 | 1-4-1-1 | Detrend only | 412 | 2.081 | 0.923 | 0.913 | 2.215 |
| 201 | 1-4-10-8 | Standard MSC | 412 | 2.000 | 0.929 | 0.908 | 2.279 |
| 206 | 1-5-1-1 | SNV only | 412 | 2.060 | 0.925 | 0.911 | 2.243 |
| 219 | 1-5-10-8 | SNV and Detrend | 412 | 1.973 | 0.931 | 0.912 | 2.234 |
| 229 | 1-6-1-1 | Standard MSC | 412 | 2.019 | 0.928 | 0.909 | 2.268 |
| 241 | 1-6-10-2 | SNV only | 412 | 1.988 | 0.930 | 0.910 | 2.255 |
| 250 | 1-7-1-1 | Standard MSC | 412 | 1.988 | 0.930 | 0.910 | 2.259 |
| 262 | 1-7-10-10 | SNV only | 412 | 2.004 | 0.929 | 0.907 | 2.288 |
| 268 | 1-8-1-1 | SNV and Detrend | 412 | 2.009 | 0.928 | 0.912 | 2.232 |
| 283 | 1-8-10-4 | Standard MSC | 412 | 1.993 | 0.930 | 0.909 | 2.273 |
| 292 | 1-9-1-1 | Standard MSC | 412 | 1.994 | 0.929 | 0.909 | 2.262 |
| 303 | 1-9-10-5 | SNV and Detrend | 412 | 1.971 | 0.931 | 0.911 | 2.241 |
| 311 | 1-10-1-1 | SNV and Detrend | 412 | 1.979 | 0.931 | 0.912 | 2.231 |
| 324 | 1-10-10-1 | Standard MSC | 412 | 1.972 | 0.931 | 0.911 | 2.238 |
| 332 | 2-1-1-1 | SNV only | 412 | 2.122 | 0.920 | 0.898 | 2.403 |
| 345 | 2-1-10-5 | SNV and Detrend | 412 | 2.007 | 0.929 | 0.918 | 2.156 |
| 355 | 2-2-1-1 | Standard MSC | 412 | 2.044 | 0.926 | 0.901 | 2.368 |
| 358 | 2-2-5-1 | None | 412 | 2.060 | 0.925 | 0.909 | 2.266 |
| 367 | 2-2-10-8 | SNV only | 412 | 2.020 | 0.928 | 0.916 | 2.177 |
| 376 | 2-3-1-1 | Standard MSC | 412 | 2.021 | 0.928 | 0.906 | 2.305 |
| 388 | 2-5-5-1 | SNV only | 412 | 1.997 | 0.929 | 0.917 | 2.163 |
| 397 | 2-5-10-8 | Standard MSC | 412 | 2.002 | 0.929 | 0.913 | 2.223 |
| 404 | 2-6-1-1 | Standard MSC | 412 | 1.985 | 0.930 | 0.912 | 2.228 |
| 411 | 2-6-10-6 | Standard MSC | 412 | 2.002 | 0.929 | 0.913 | 2.221 |
| 415 | 2-7-1-2 | SNV and Detrend | 412 | 2.008 | 0.928 | 0.918 | 2.158 |
| 425 | 2-7-10-3 | Standard MSC | 412 | 2.001 | 0.929 | 0.913 | 2.218 |
| 432 | 2-8-1-1 | Standard MSC | 412 | 1.997 | 0.929 | 0.913 | 2.219 |
| 439 | 2-9-5-3 | Standard MSC | 412 | 2.001 | 0.929 | 0.913 | 2.220 |
| 446 | 2-10-10-1 | Standard MSC | 412 | 2.003 | 0.929 | 0.911 | 2.241 |

[a]SEC: Standard error of calibration
[b]R²: Coefficient of determination in calibration
[c]1-VR: 1-variance ratio (one minus the ratio of unexplained variance to total variance)
[d]SECV: Standard error of cross-validation MPLS, which is one of regression analysis methods, was used to design optimal NIRS calibration equations. As a result, in the case of carbohydrate, when a weighted multiplicative scatter correction (MSC) as a scatter correction method and a math treatment of 1-4-5-1 (1st derivatives, 4 nm gap, 5 points smoothing, 1 point second smoothing) were applied to the primitive spectrum, the greatest coefficient of determination value of 0.971 and the lowest standard error (SEC) value of 4.066 were able to be obtained, from among when other scattering methods and math treatment conditions were used.

In the case of protein, when standard MSC as a scatter correction method and the math treatment of 2-5-5-3 (2nd derivative, 5 nm gap, 5 points smoothing, 3 points second smoothing) were applied to the primitive spectrum, the greatest coefficient of determination ($R^2$) value of 0.974 and the lowest calibration equation standard error (SEC) value of 1.080 were able to be obtained, from among when other scattering methods and math treatment conditions were used.

In the case of fat, when standard normal variate (SNV) correction as a scatter method and the math treatment of 1-1-1-1 (1st derivatives, 1 nm gap, 1 point smoothing, 1 point second smoothing) were applied to the primitive spectrum, the greatest coefficient of determination value of 0.937, and the lowest calibration equation standard error value of 1.890 were able to be obtained.

(iii) Constructing of Calibration Equations by Using 162 Foods or Agricultural Sources for Validation To evaluate whether NIRS primary calibration equations selected by using 412 foods or agricultural sources having different physicochemical properties and compositions are applicable to unknown foods or agricultural sources, 162 foods or agricultural sources which were not used in selecting the NIRS primary calibration equations were used for validation. A monitor program of WinISI II software was used, and the applicability and accuracy of calibration equations with respect to known samples were validated based on statistic values of standard error of prediction (SEP), $R^2$ (coefficient of determination in prediction), bias (an average difference between reference and NIRS values), and standard deviation (SD).

TABLE 5

Primary calibration equations were validated by using 162 foods or agricultural sources for validation to determine calibration equations that are optimal for content analysis of nutritional components (carbohydrate, protein, and fat) in a plurality of foods or agricultural sources having different physicochemical properties and compositions

| Nutritional components | Scatter correction method | Math treatment | Calibration SEC | $R^2$ | Cross validation 1-VR | SECV |
|---|---|---|---|---|---|---|
| Carbohydrate | Weighted MSC | 1-4-5-1 | 4.066 | 0.971 | 0.961 | 4.685 |
|  |  | 1-4-10-5 | 4.177 | 0.969 | 0.961 | 4.706 |
|  |  | 1-4-1-1 | 4.066 | 0.964 | 0.959 | 4.817 |
| Protein | Standard MSC | 2-5-5-3 | 1.087 | 0.974 | 0.940 | 1.645 |
|  |  | 2-6-1-1 | 1.136 | 0.971 | 0.935 | 1.715 |
|  |  | 2-5-10-1 | 1.183 | 0.969 | 0.936 | 1.705 |
| Fat | SNV | 1-1-1-1 | 1.890 | 0.937 | 0.914 | 2.204 |
|  |  | 1-3-10-5 | 1.987 | 0.930 | 0.910 | 2.253 |
|  |  | 1-1-3-1 | 2.050 | 0.925 | 0.912 | 2.234 |

TABLE 6

Validation results on optimal NIRS calibration equations by using 162 foods or agricultural sources having different physicochemical properties and compositions

| Nutritional components | Number of samples | Average | Standard deviation | Bias | Coefficient of determination | SEP | Slope |
|---|---|---|---|---|---|---|---|
| Carbohydrate | 162 | 23.331 | 22.054 | −0.345 | 0.987 | 2.515 | 0.991 |
| Protein | 162 | 8.979 | 6.544 | −0.042 | 0.970 | 1.144 | 1.012 |
| Fat | 162 | 5.116 | 5.875 | −0.255 | 0.947 | 1.370 | 0.966 |

Standard deviation: Standard deviation (SD)
Bias: Average difference between reference and NIRS values
Coefficient of determination ($R^2$): Coefficient of determination in prediction
Standard error (SEP(C)): Corrected Standard error of prediction
Slope: Steepness of a straight line curve Coefficient of determination and standard errors of prediction were used as a reference to determine the accuracy of predicted values obtained by NIRS calibration equations. When optimal NIRS calibration equations were applied to unknown samples, in the case of carbohydrate, the coefficient of determination was 0.987, which is greater than 0.971 being the coefficient of determination of the corresponding calibration equation for calibration, and the standard error of prediction was 2.515, which is lower than 4.066 being the standard error of the corresponding calibration equation for calibration. This results show that predicted values of unknown samples can be more accurately analyzed. In the case of a protein, the coefficient of determination was 0.970, which is slightly smaller than 0.974 being the coefficient of determination of the corresponding calibration equation for calibration, and the standard error of prediction was 1.144, which is smaller than 1.404 being 1.3 times as great as 1.080 that is the standard error of the corresponding calibration equation for calibration. In the case of fat, the coefficient of determination was 0.947, which is higher than 0.01 being the coefficient of determination of the corresponding calibration equation for calibration, and the standard error of prediction was 1.370, which is lower than 1.890 being the standard error of the corresponding calibration equation for calibration. Thus, it was confirmed that the calibration equations are effectively applicable to the content analysis of unknown samples (foods or agricultural sources).

Figure 9:
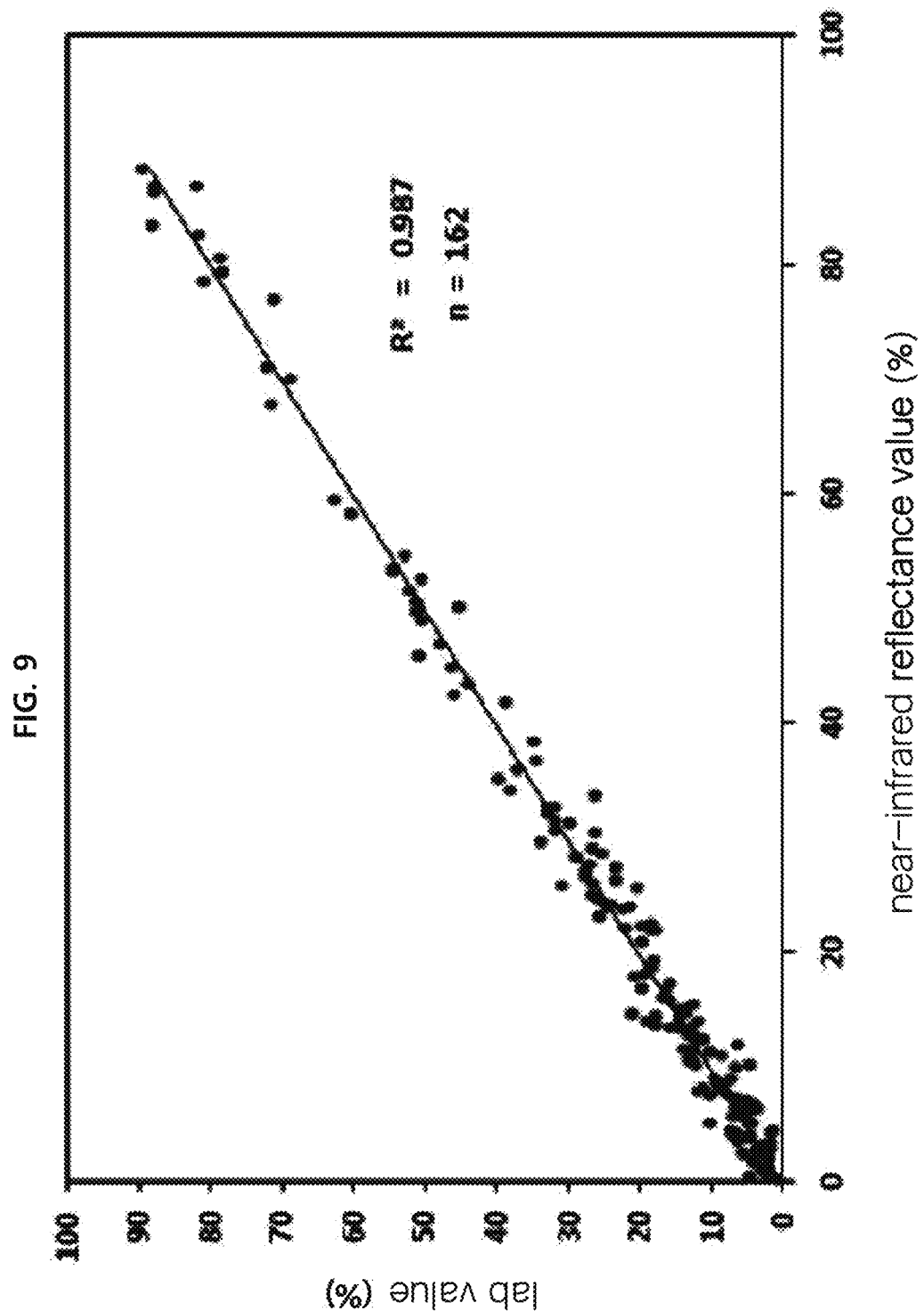
FIG. 9 shows a scatter diagram to compare carbohydrate contents in 412 foods belonging to the calibration sample set and having different physicochemical properties and compositions obtained from the near-infrared absorption spectra thereof with carbohydrate contents in 162 foods that belong to the validation sample set obtained from near-infrared absorption spectra of the 162 foods.
Figure 10:
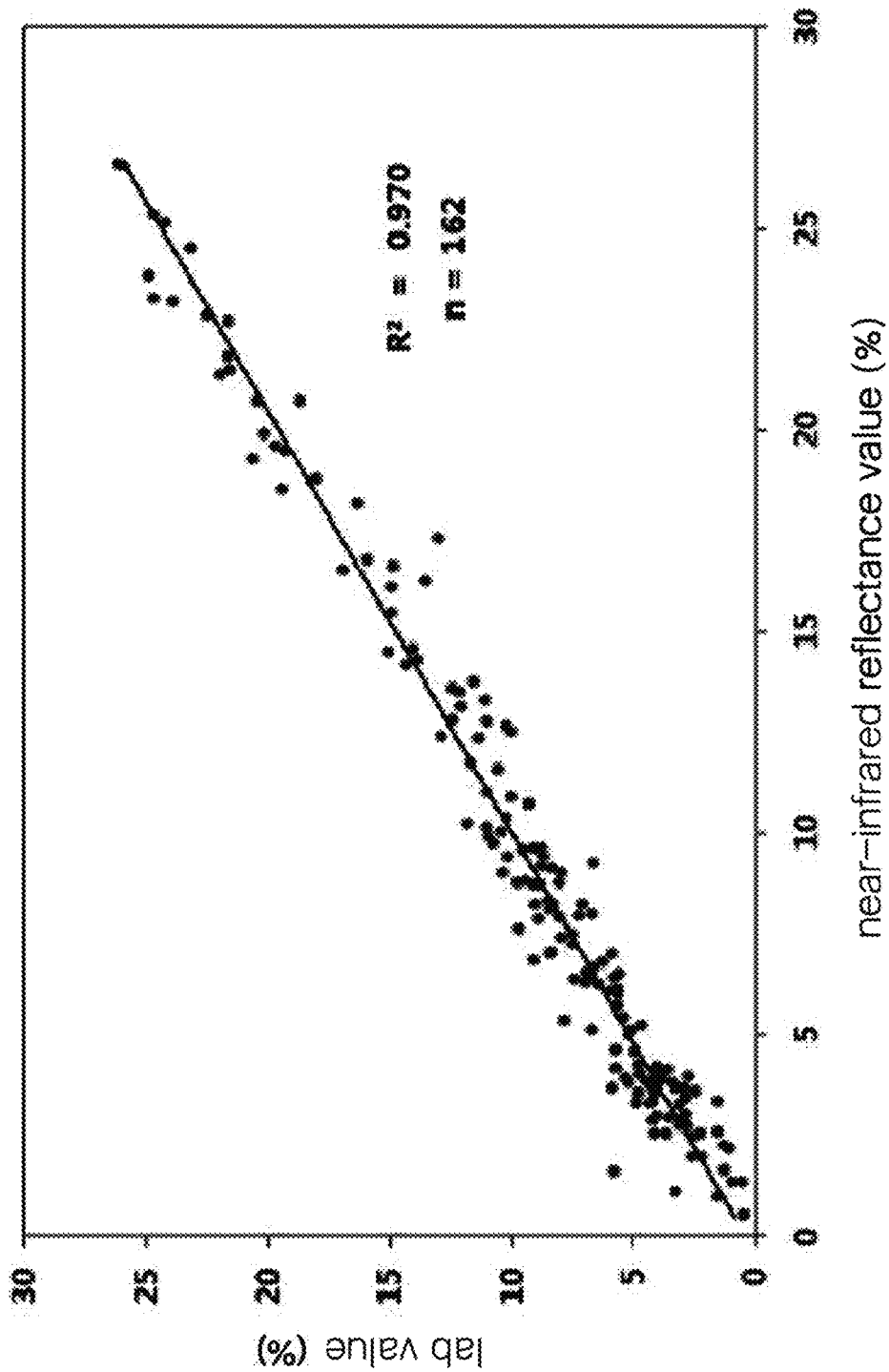
FIG. 10 shows a scatter diagram to compare protein contents in foods belonging to the calibration sample set and having different physicochemical properties and compositions obtained from the near-infrared absorption spectra thereof with protein contents in 162 foods that belong to the validation sample set obtained from near-infrared absorption spectra of the 162 foods.
Figure 11:
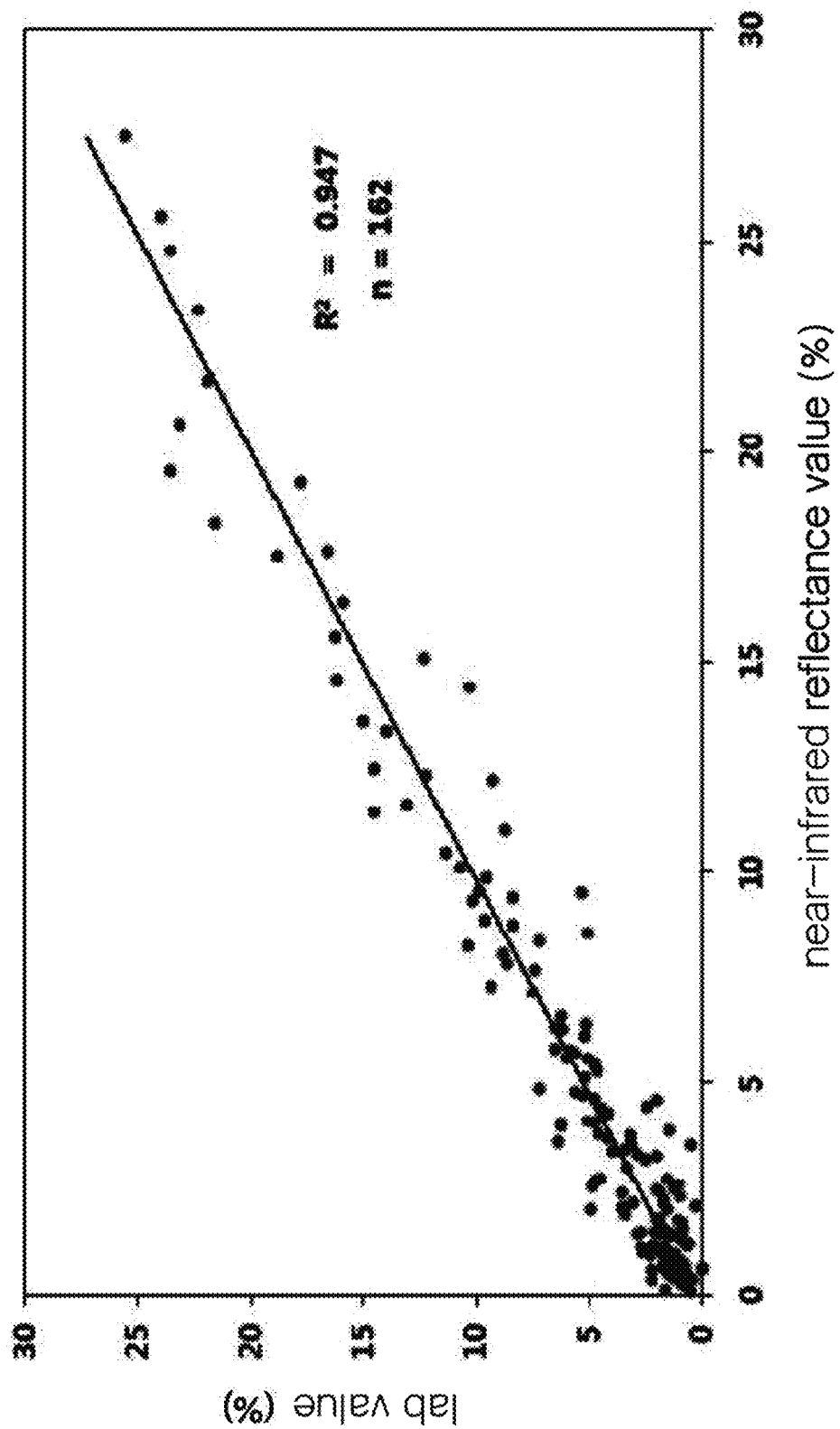
FIG. 11 shows a scatter diagram to compare fat contents in 412 foods belonging to the calibration sample set and having different physicochemical properties and compositions obtained from the near-infrared absorption spectra thereof with fat contents in 162 foods that belong to the validation sample set obtained from near-infrared absorption spectra of the 162 foods.

Carbohydrate, protein, and fat contents in 412 foods or agricultural sources for calibration, having different physicochemical properties and compositions, obtained based on near-infrared absorption spectra thereof were compared with carbohydrate, protein, and fat contents in 162 foods or agricultural sources for validation obtained based on near-infrared absorption spectra thereof. Results thereof are shown in the scatter diagram shown in FIGS. 9 to 11.

What is claimed is:
1. A method of simultaneously analyzing amounts of a plurality of nutritional components in a plurality of foods or agricultural sources having different physicochemical properties and compositions by near-infrared reflectance spectroscopy, the method comprising:
(1) analyzing an amount of a nutritional component contained in a plurality of various species of foods and agricultural sources having different physicochemical properties and compositions by using analytical methods of analyzing components described in Korean Food Standard Codex;
(2) classifying the plurality of various species of foods or agricultural sources into a calibration sample set and a validation sample set;
(3) irradiating a near-infrared ray to the calibration sample set and the validation sample set to simultaneously obtain primitive near-infrared absorption spectra thereof;
(4) correcting scatter of the primitive near-infrared absorption spectrum of the calibration sample set obtained in the step (3);
(5) obtaining a derivative based on the primitive absorption spectrum of which scatter has been corrected, followed by subjecting the derivative to a math treatment represented by W-X-Y-Z where W is a differentiation degree, X is a gap (nm) of wavelength used to measure a spectrum, Y is a primary smoothing to smooth the connection of the spectrum during a math treatment with respect to the gap of wavelength, Z is a secondary smoothing to smooth the connection of the spectrum during the math treatment with respect to the gap of wavelength, and performing statistical analysis on the resultant derivative by comparing content values obtained based on the resultant derivative with content values obtained by using the analytical methods obtained in the step (1), thereby selecting primary calibration equations;

(6) validating the primary calibration equations selected in the step (5) by applying the primary calibration equations to the primitive near-infrared absorption spectra of the validation sample set obtained in the step (3) to obtain an optimal calibration equation; and (7) quantitatively analyzing the nutritional component in the plurality of various foods or agricultural sources having different physicochemical properties and compositions by using the optimal calibration equation.

2. The method of claim 1, wherein the plurality of various foods or agricultural sources having different physicochemical properties and compositions have at least one form selected from the group consisting of solid, liquid, and viscous semi-solid.

3. The method of claim 1, wherein a ratio of the number of samples constituting the calibration sample set to the number of samples constituting the validation sample set in the step (2) is in a range of 2:1 to 3:1.

4. The method of claim 1, wherein the near-infrared ray is irradiated by a horizontal direct contact food analyzer (DCFA) module, and the various foods or agricultural sources having different physicochemical properties and compositions are placed in a measurement vessel that is a cover-free, and transparent reflective vessel.

5. The method of claim 1, wherein the nutritional component comprises at least one selected from the group consisting of a protein, a carbohydrate, a sugar, a fat, a fatty acid, an amino acid, an organic acid, a moisture, a vitamin, and a mineral.

6. The method of claim 1, wherein the primitive near-infrared absorption spectra are obtained in a range of 400 nm to 2,500 nm.

7. The method of claim 1, wherein a mode to measure the near-infrared absorption spectra is any one mode selected from the group consisting of a diffuse reflectance mode, a transmission-reflectance mode, and a transmission mode.

8. The method of claim 1, wherein the near-infrared absorption spectrum is corrected by using at least one method selected from the group consisting of standard multiplicative scattering correction (standard MSC), inverse MSC, detrend correction, standard normal variate (SNV) correction, and weighted MSC.

9. The method of claim 1, wherein the statistical analysis performed on the resultant derivative is a multivariate regression analysis.

10. The method of claim 9, wherein the multivariate regression analysis is any one selected from the group consisting of multiple linear regression (MLR), principal component regression (PCR), partial least squares (PLS), and modified partial least squares (MPLS).

11. The method of claim 1, wherein, when the nutritional component is carbohydrate, the scatter is corrected by weighted multiplicative scattering correction (weighed MSC), and the math treatment is selected from the group consisting of 1-4-5-1, 1-4-1-1, and 1-4-10-5.

12. The method of claim 1, wherein, when the nutritional component is protein, the scatter is corrected by standard multiplicative scattering correction (standard MSC), and the math treatment is selected from the group consisting of 2-5-5-3, 2-5-10-1 and 2-6-1-1.

13. The method of claim 1, wherein, when the nutritional component is fat, the scatter is corrected by standard normal variate (SNV) correction, and the math treatment is selected from the group consisting of 1-1-1-1, 1-1-3-1, and 1-3-10-5.

* * * * *

UNITED STATES PATENT AND TRADEMARK OFFICE
CERTIFICATE OF CORRECTION

PATENT NO. : 10,073,032 B2
APPLICATION NO. : 15/272696
DATED : September 11, 2018
INVENTOR(S) : Myoung-Gun Choung Page 1 of 1

It is certified that error appears in the above-identified patent and that said Letters Patent is hereby corrected as shown below:

On the Title Page

Item (73) assignee reads:
KNY-INDUSTRY COOPERATION FOUNDATION, Gangwon-do (KR)

Should be corrected to read:
KNU-INDUSTRY COOPERATION FOUNDATION, Gangwon-do (KR)

Signed and Sealed this
Thirtieth Day of October, 2018

Andrei Iancu
*Director of the United States Patent and Trademark Office*